United States Patent [19]
Dreyfuss et al.

[11] Patent Number: 6,013,627
[45] Date of Patent: Jan. 11, 2000

[54] ORGANIC COMPOUNDS

[75] Inventors: Michael Morris Dreyfuss, Basel, Switzerland; Carolyn Ann Foster, Vienna, Austria; Hans-Ulrich Naegeli, Arlesheim, Switzerland; Berndt Oberhauser, Vienna, Austria

[73] Assignee: Novartis AG, Basel, Switzerland

[21] Appl. No.: 08/776,440

[22] PCT Filed: Jul. 26, 1995

[86] PCT No.: PCT/EP95/02966

§ 371 Date: Jan. 24, 1997

§ 102(e) Date: Jan. 24, 1997

[87] PCT Pub. No.: WO96/03430

PCT Pub. Date: Feb. 8, 1996

[30] Foreign Application Priority Data

Jul. 27, 1994 [GB] United Kingdom .................... 9415168
Mar. 3, 1995 [GB] United Kingdom .................... 9504332

[51] Int. Cl.[7] .......................... A61K 38/00; A61K 38/12; C07K 5/00; C07K 7/00
[52] U.S. Cl. ................................................. 514/9; 530/317
[58] Field of Search ................... 530/317; 514/9

[56] References Cited

U.S. PATENT DOCUMENTS

| | | | |
|---|---|---|---|
| 4,425,428 | 1/1984 | Weingarten | 530/328 |
| 4,443,367 | 4/1984 | Weingarten | 530/328 |
| 5,116,816 | 5/1992 | Dreyfuss et al. | 514/11 |
| 5,643,869 | 7/1997 | Dreyfuss et al. | 514/9 |

OTHER PUBLICATIONS

Derwent Abstract JP07109229–A + English Translation.

*Primary Examiner*—Avis M. Davenport
*Attorney, Agent, or Firm*—Carol A. Loeschorn

[57] ABSTRACT

Cyclopeptolides of formula I

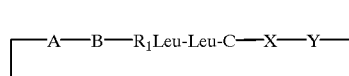

wherein A, B, R, Leu, Leu, C, X and Y are as defined, are inhibitors of adhesion molecule expression and are thus useful for treatment of inflammatory and other diseases which involve increased levels of adhesion molecule expression.

30 Claims, 7 Drawing Sheets

ORGANIC COMPOUNDS

This invention relates to cyclopeptolides and to their therapeutic use as inhibitors of adhesion molecule expression.

Cellular adhesion molecules such as ICAM-1, VCAM-1 and E-selectin are expressed on the surface of endothelial cells, as well as keratinocytes for ICAM-1, in response to pro-inflammatory mediators including TNFα, IFNγ, IL1 and LPS. Corresponding counter-ligands, e.g. LFA-1, VLA-4 and $SLE^x$, are expressed on the surfaces of circulating blood cells. Transendothelial migration of leucocytes during inflammatory processes, as well as extravascular cell-cell interactions, are regulated as a result of the interactions between these adhesion molecules and their counterligands. Consequently, inhibitors of adhesion molecule expression offer potential for the treatment of many disease states. However, no suitable low molecular weight inhibitors of adhesion molecule expression are currently available.

Cyclopeptolides are cyclic molecules comprising amino acid residues linked together by peptide bonds and at least one hydroxy substituted carboxylic acid residue which is linked through its hydroxyl substituent to the neighbouring acid residue by an ester linkage.

We have now discovered a new class of cyclopeptolides which are inhibitors of ICAM-1, VCAM-1 and E-selectin expression.

The present invention provides cycloheptapeptolides of formula I

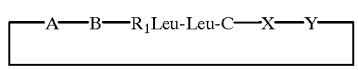
I wherein:
- A is an α-hydroxy-substituted butyric acid residue optionally γ-substituted by $R_6$, which represents CN, $COOR_2$, $CONR_3R_4$, $COR_5$, $CSNH_2$ or alkyl, which may be substituted by azido, halogen, alkoxy, optionally protected hydroxy or amino, vinyl, which may be substituted by alkyl, halogen or CN, cycloalkyl, tetrazolyl or —C≡CH, wherein $R_2$ represents hydrogen or optionally arylsubstituted alkyl, $R_3$ and $R_4$ are the same or different and represent hydrogen or alkyl or form together with the nitrogen a 3- to 6-membered ring optionally containing a second heteroatom, and $R_5$ represents hydrogen or lower alkyl,
- B is an α-amino-γ-methyl-substituted octanoic acid residue;
- $R_1$ is hydrogen or methyl;
- C is a tryptophan or N-methyl-tryptophan residue of formula VI

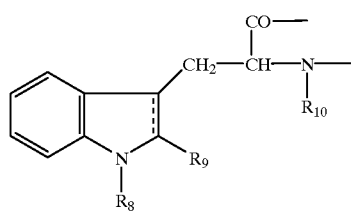
VI wherein $R_8$ represents hydrogen, alkoxy, alkyl or benzyl, $R_9$ represents hydrogen or halogen, $R_{10}$ represents hydrogen or methyl and ---- represents a single or double bond, X is an α-amino-substituted ($C_2$ to $C_{14}$) carboxylic acid residue, and Y is an α-amino- or N-methyl-α-amino substituted ($C_2$ to $C_{10}$) carboxylic acid residue.

In formula I the C-terminal to N-terminal orientation of the amino acid residues is in the clockwise direction, and the peptolide ester bond is between residues A and Y. When $R_1$ is methyl, the residues $R_1$-Leu and Leu are N-methyl-leucine and leucine residues respectively.

Preferably A is an α-hydroxybutyric acid residue, which is γ-substituted by cyano, $COOR_2'$, whererby $R_2'$ represents hydrogen, lower alkyl with 1 to 4 carbon atoms or diphenylmethyl, $CONR_3'R_4'$, whereby $R_3'$ represents hydrogen or methyl and $R_4'$ represents hydrogen or alkyl or $R_3'$ and $R_4'$ form together with the nitrogen a 3- to 6-membered ring or a morpholinyl ring, $CH_2OH$, $COR_5'$, whereby $R_5'$ represents hydrogen or lower alkyl with 1 to 4 carbon atoms, vinyl optionally substituted by CN, Br or lower alkyl with 1 to 4 carbon atoms, alkyl optionally substituted by azido, amino, hydroxy, chloro or alkoxy, tetrazolyl, cyclopropyl, $CSNH_2$ or —C≡CH.

Preferably C is a N-methyltryptophan residue of formula VI, wherein $R_8$ represents hydrogen, ($C_1$ to $C_4$)alkoxy, especially methoxy, or alkyl and $R_9$ represents hydrogen or halogen.

Preferably X is an α-amino-substituted ($C_4$ to $C_8$) carboxylic acid residue, which is optionally β- or γ-($C_1$ to $C_4$) alkyl substituted. Most preferably X is an α-amino-β- or γ-($C_1$ to $C_4$) alkyl-, especially methyl-, substituted octanoic or a butyric acid residue.

Preferably Y is an N-methyl-α-amino-substituted ($C_2$ to $C_4$) carboxylic acid residue, which is optionally β- or γ-($C_1$ to $C_4$) alkyl-substituted. Most preferably Y is an N-methyl-alanine or N-methyl-valine residue.

The compounds of formula I comprise asymmetric C-atoms and these may be in either the R or S configuration.

The invention includes open chain peptides or peptolides corresponding to the compounds of formula I; for instance, the open chain molecules obtained by either cleavage of the ester bond between residues Y and A or cleavage of an amide linkage between any other adjacent pair of the acid residues. Preferred open-chain derivatives are compounds of formulae IV and V

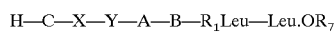
IV and

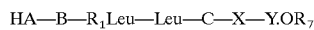
V wherein $R_7$ represents hydrogen or alkyl.

A preferred subgroup of compounds of the invention is the compounds of formula Ip

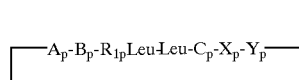
Ip wherein:
- $A_p$ is an α-hydroxy-substituted butyric acid residue optionally γ-substituted by $R_{6p}$, which represents CN, optionally protected $CH_2OH$, $COOR_{2p}$, $CONR_{3p}R_{4p}$, $COR_{5p}$ or —CH=$CH_2$, whereby $R_{2p}$ represents hydrogen or optionally arylsubstituted alkyl, $R_{3p}$ and $R_{4p}$ are the same or different and represent hydrogen or alkyl or form together with the nitrogen a 5- or 6-membered ring optionally containing a second heteroatom, and $R_{5p}$ represents hydrogen or lower alkyl, $B_p$ is an α-amino-γ-methyl-substituted octanoic acid residue;

$R_{1p}$ is hydrogen or methyl;

$C_p$ is a tryptophan or N-methyl-tryptophan residue, which is optionally N'-($C_1$ to $C_4$) alkoxy substituted;

$X_p$ is an α-amino-substituted ($C_2$ to $C_{14}$) carboxylic acid residue, and $Y_p$ is an α-amino- or N-methyl-α-amino substituted ($C_2$ to $C_{10}$) carboxylic acid residue.

A further subgroup of compounds of the invention are the compounds of formula I'p

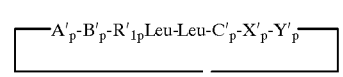

I'p wherein:

$A'_p$ is an α-hydroxy-substituted butyric acid residue optionally γ-substituted by $R'_{6p}$, which represents CN, $COOR'_{2p}$, $CONR'_{3p}R'_{4p}$, $COR'_{5p}$, alkyl, which may be substituted by azido, halogen, alkoxy, optionally protected hydroxy or amino, vinyl, which may be substituted by alkyl, halogen or CN, cycloalkyl, tetrazolyl or —C≡CH, whereby $R'_{2p}$ represents hydrogen or optionally arylsubstituted alkyl, $R'_{3p}$ and $R'_{4p}$ are the same or different and represent hydrogen or alkyl or form together with the nitrogen a 3- to 6-membered ring optionally containing a second heteroatom, and $R'_{5p}$ represents hydrogen or lower alkyl, $B'_p$ is an α-anino-γ-methyl-substituted octanoic acid residue;

$R'_{1p}$ is hydrogen or methyl;

$C'_p$ is a tryptophan or N-methyl-tryptophan residue of formula

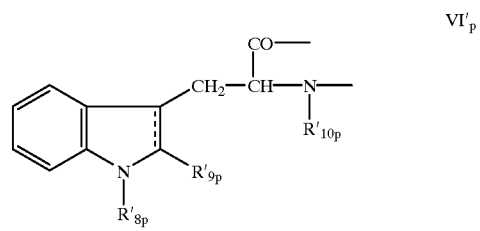

VI'p wherein $R'_{8p}$ represents hydrogen, alkoxy, alkyl or benzyl, $R'_{9p}$ represents hydrogen or halogen, $R'_{10p}$ represents hydrogen or methyl and ---- represents a single or double bond, $X'_p$ is an α-amino-substituted ($C_2$ to $C_{14}$) carboxylic acid residue, and $Y'_p$ is an α-amino- or N-methyl-α-amino substituted ($C_2$ to $C_{10}$) carboxylic acid residue.

Also the invention includes all the compounds of the invention when in salt or ester form as well as in free form.

The compounds of formulae II and III (hereinafter referred to as compounds A and B respectively)

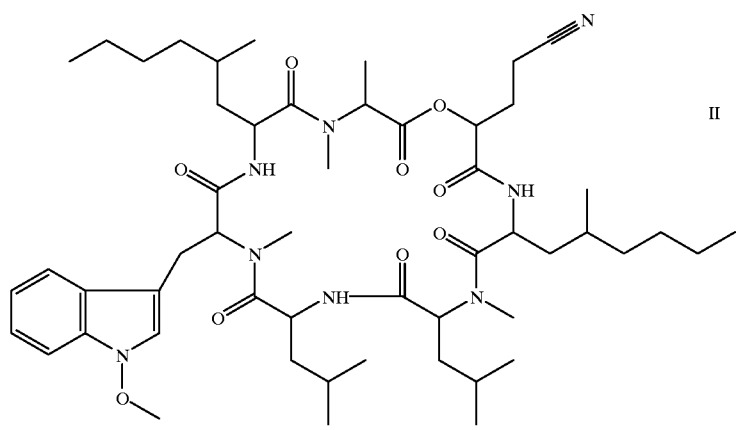

(A)

II

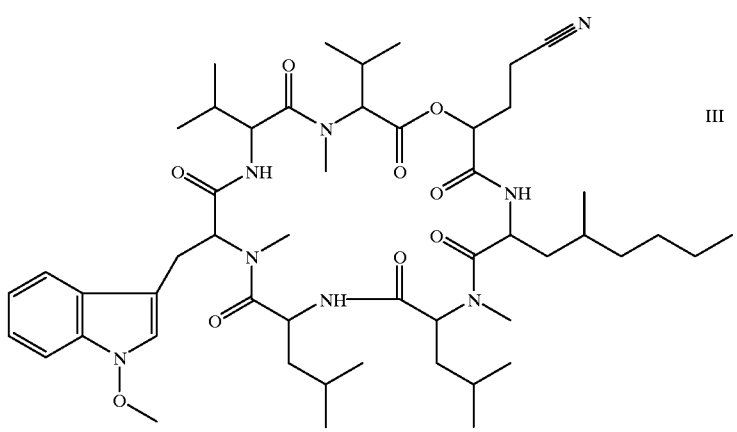

-continued (B)

III have been isolated from cultures of fungal strain F924471/08 which was isolated from a leaf litter sample collected near La Plata, Argentina and is tentatively assigned to the genus Bartalinia. Samples of strain F92-4471/08 were deposited with the US Department of Agriculture, NRRL culture collection under the provisions of the Budapest Treaty on Jul. 2, 1993 and are identified as deposit number NRRL 21123. The characteristics of fungal strain F92-4471/08 are described hereinafter in Example 1.

The invention includes the strain F92-4471/08 (NRRL 21123) in isolated form and mutants and derivatives thereof as well as all novel cyclopeptolides which are produced by this strain.

The compounds A and B and related compounds may be obtained by cultivating F92-4471/08/NRRL 21123 or a mutant or derivative thereof or similar fungal species in nutrient medium and recovering the compounds therefrom, for example as described in Example 2.

The characteristics of the compounds A and B are given in Example 3.

Compounds according to the invention may be prepared by derivatisation of the compounds A and B, which comprises a)—for the preparation of compounds of formula I, wherein $R_6$ represents $COOR_2'$, whereby $R_2'$ is alkyl optionally substituted by aryl, reacting compounds of formula I, wherein $R_6$ represents CN, with nucleophiles, preferentially an alcohol, with appropriate basic or acidic catalysis, preferentially hydrochloric acid, in organic solvents, preferentially ether, or b)—for the preparation of compounds of formula I, wherein $R_6$ represents COAlkyl, reacting compounds of formula I, wherein $R_6$ represents CN, using as nucleophiles organo-metallic compounds, preferentially Grignard compounds or lithio-alkyls, which are reacted in aprotic organic solvents, preferentially ethers, with or without catalysts, or c)—for the preparation of compounds of formula I, wherein $R_6$ represents COOH, hydrolyzing compounds of formula I, wherein $R_6$ represents COOAlkyl, with mineral acid, preferentially hydrochloric acid in aqueous alcoholic solution or base, or d)—for the preparation of compounds of formula I, wherein $R_6$ represents $COOR_2'$, esterifying compounds of formula I, wherein $R_6$ represents COOH, by standard methods, preferentially by conversion into the acid chloride with e.g. thionyl chloride and treatment with an appropriate alcohol in the presence or absence of an acid binder, or e)—for the preparation of compounds of formula I, wherein $R_6$ represents $CH_2OH$, reducing compounds of formula I, wherein $R_6$ represents $COOR_2$, with metal hydrides or boron hydrides, preferentially borane dimethylsulfide complex, in organic solvents, or f)—for the preparation of compounds of formula I, wherein $R_6$ represents $CONR_3R_4$, transforming compounds of formula I, wherein $R_6$ represents $COOR_2$, by reaction with amines, preferentially by conversion of the free acid into the acid chloride and reaction with the amine $HNR_3R_4$, or g)—for the preparation of compounds of formula I, wherein $R_6$ represents CHO, oxidizing compounds of formula I, wherein $R_6$ represents $CH_2OH$, or h)—for the preparation of compounds of formula I, wherein $R_6$ represents optionally substituted vinyl, reacting compounds of formula I, wherein $R_6$ represents CHO, with a methyl-Wittig reagent, or i)—for the preparation of compounds of formula I, wherein $R_6$ represents optionally substituted alkyl, reacting compounds of formula I, wherein $R_6$ represents $CH_2OH$, or j)—for the preparation of compounds of formula I, wherein $R_6$ represents $CH_2NH_2$, reducing compounds of formula I, wherein $R_6$ represents $CH_2N_3$, or k)—for the preparation of compounds of formula I, wherein $R_1$ represents $C\equiv CH$, reacting compounds of formula I, wherein $R_6$ represents $CH{=}CBr_2$, or l)—for the preparation of compounds of formula I, wherein $R_6$ represents cyclopropyl, reacting compounds of formula I, wherein $R_6$ represents vinyl, with diazomethane, or m)—for the preparation of compounds of formula I, wherein $R_6$ represents tetrazolyl, reacting compounds of formula I, wherein $R_6$ is CN, with an azide-compound, or n)—for the preparation of compounds of formula I, wherein $R_8$ represents hydrogen, removing the methoxy from compounds of formula I, wherein $R_8$ represents $OCH_3$, or o)—for the preparation of compounds of formula I, wherein the symbol ---- represents a single bond, reducing compounds of formula I, wherein the symbol ---- represents a double bond, or p)—for the preparation of compounds of formula I, wherein $R_8$ represents alkyl or benzyl, introducing these groups into compounds of formula I, wherein $R_8$ represents hydrogen, or q)—for the preparation of compounds of formula I, wherein $R_9$ represents halogen, halogenating compounds of formula I, wherein $R_9$ represents hydrogen, or r)—for the preparation of compounds of formula I, wherein $R_8$ represents alkoxy and the symbol ---- represents a double bond, reacting compounds of formula I, wherein $R_8$ represents hydrogen and the symbol ---- represents a single bond, with an alkali tungstate and hydrogen peroxide and alkylating the N-hydroxy-indol-intermediate, or s)—for the preparation of compounds of formula I, wherein $R_6$ represents $CSNH_2$, reacting compounds of formula I with sulfur derivatives, preferentially with diphenylphosphinodithioic acid.

The compounds of the invention may be prepared also by chemical synthesis; for example, using conventional peptide synthesis techniques. Typically the final step in the preparation of the compounds is a cyclisation step in which a linear peptide or peptolide comprising the acid residues A, B, $R_1$Leu, Leu, C, X and Y linked together in appropriate order is cyclised by an amide- or ester-bond forming reaction.

Thus the invention includes a process for the preparation of a cyclic peptolide of formula I comprising cyclisation of a linear peptide or peptolide comprising the acid residues A, B, $R_1$Leu, Leu, C, X and Y linked together in appropriate order.

The compounds of the invention exhibit pharmacological activity and are therefore useful as pharmaceuticals. In particular the compounds are inhibitors of the stimulated expression of cellular adhesion molecules, especially inhibitors of VCAM-1 relative to E-selectin and ICAM-1 expression. The effect on VCAM-1 inhibition occurs at both transcriptional and posttranscriptional level. Assays which may be used to detect the inhibition of ICAM-1, VCAM-1 and E-selectin expression by the compounds of the invention are described after the Examples. Thus the compounds are useful for the treatment or prophylaxis of disease processes which involve expression of cellular adhesion molecules. These disease processes include many acquired and inherited diseases/disorders where leucocyte trafficing plays a prominent role in the pathogenic process, most notably acute and chronic inflammation (e.g. allergy, asthma, psoriasis, reperfusion injury, rheumatoid arthritis and septic shock) and autoimmune states (e.g. multiple sclerosis). Other indications for the compounds of the invention include tumour metastasis (e.g. melanoma, osteocarcinoma) and allograft/xenograft rejection, since it is known that inhibition of vascular adhesion molecules can greatly improve the prognosis of these processes.

Also the compounds of the invention have therapeutic potential in hyperproliferative skin diseases (e.g. psoriasis) as well as various malignancies in view of their inhibitory activity at submicromolar concentrations when tested for 72 hours in a keratinocyte-based as well as other proliferation assays.

The compounds of the invention are active in inhibiting TNFα- or IL6-induced HIV production in the U1 monocytic cell line, as evaluated by p24 Elisa and are therefore also useful in the treatment of immunodeficiences and virally caused diseases, especially in the treatment of AIDS.

Thus the invention also includes the therapeutic use of, and therapeutic compositions containing, the compounds of the invention.

In particular the invention includes methods for the treatment or prophylaxis of diseases which involve expression of adhesion molecules which comprise administering a therapeutically or prophylactically effective amount of a compound according to the invention to a subject.

The invention also includes therapeutic compositions comprising a therapeutically effective amount of a compound according to the invention.

Furthermore the invention includes the use of a compound according to the invention for the preparation of a medicament for application in the treatment or prophylaxis of diseases which involve expression of adhesion molecules.

The compositions may be for parenteral, oral, aerosol or topical use and usually comprise one or more pharmaceutically acceptable carriers diluents or excipients and may comprise additives such as stabilisers and the like.

The dosages of the compounds used may be varied having regard to the condition or disease involved, whether the use is for treatment or prophylaxis thereof and the mode and route of administration among other things. In general, however satisfactory results are obtained on administration orally at dosages of from about 0.05 to about 10 mg/kg/day, preferably from about 0.1 to about 7.5 mg/kg/day, more preferably from about 0.1 to about 2 mg/kg/day administered once or, in divided doses, 2 to 4 times per day. Alternatively for parenteral administration, e.g. by iv drip or infusion, dosages from about 0.01 to about 5 mg/kg/day, preferably from about 0.05 to about 1 mg/kg/day and more preferably from about 0.1 to about 1.0 mg/kg/day may be used.

Suitable daily dosages for human patients are thus from about 2.5 to about 500 mg p.o., preferably from about 5 to about 250 mg p.o., more preferably from about 5 to about 100 mg p.o.; or from about 0.5 to about 250 mg i.v., preferably from about 2.5 to about 125 mg i.v. and more preferably from about 2.5 to about 50 mg i.v.

The compounds may be administered by any appropriate route, including enterally, parenterally and topically or by inhaler. Suitable enterally administered forms are solutions for drinking, tablets or capsules. Suitable parenteral forms are injectable solutions or suspensions. Suitable forms for topical administration include creams, lotions and the like at a concentration range of 0.01–10%, preferably from 0.1 to 1%, by weight for such formulations. Suitable unit dosage forms for oral administration may comprise from 1 to 50 mg of the compound, usually from 1 to 10 mg. The compound of example 4 in the preferred compound of the invention and may be administered to larger mammals, for example humans, by similar modes of administration at similar or lower dosages than conventionally employed with known standards for such indications.

The invention is further described, by way of illustration only, in the following examples which refer to the accompanying diagrams in which.

Figure 1:
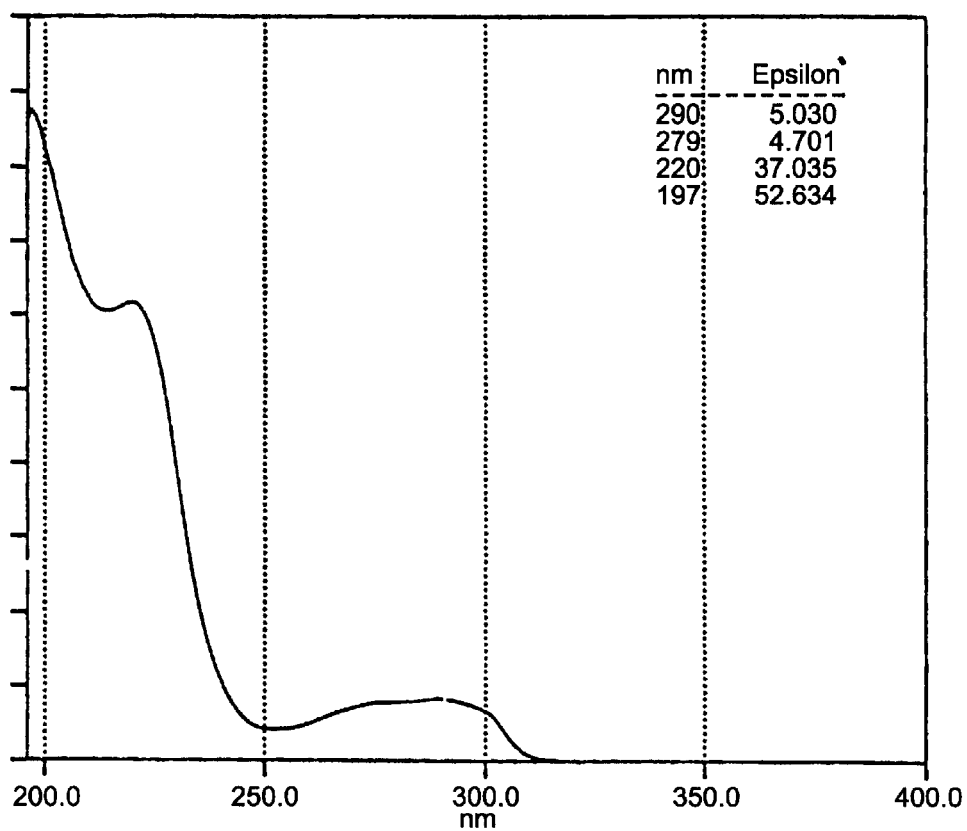
FIG. 1 shows the UV spectra of compounds A (a) and B (b)
Figure 1:
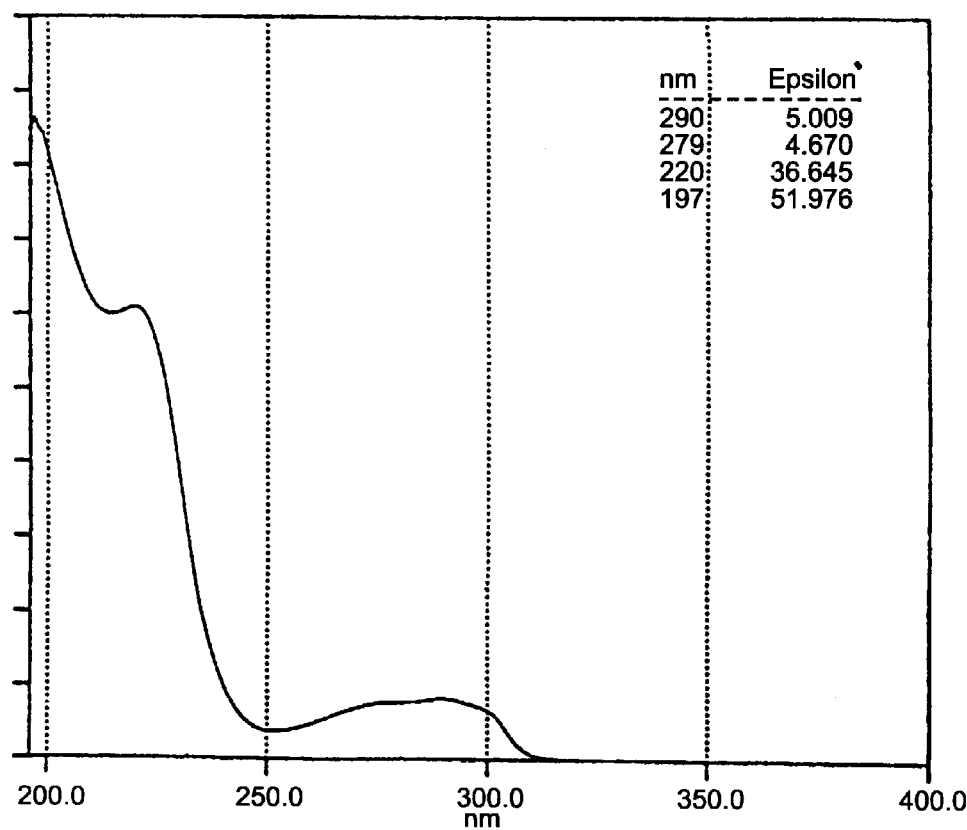

In the following examples, which illustrate the invention without limiting it, all temperatures are given in degrees Celsius and the following abbriaviations are used:

Bz = benzyl
iPr = isopropyl
nPr = n-propyl
db = double bond
sb = single bond
br = broad
d = doublet
Hba = modified 2-hydroxybutyric acid
m = multiplet
q = quartet
t = triplet
TFA = trifluoro acetic acid
THF = tetrahydrofuran

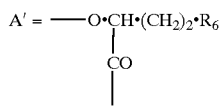

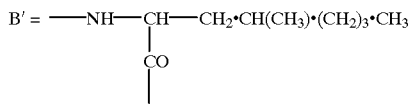

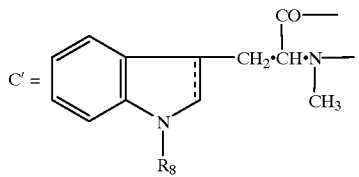

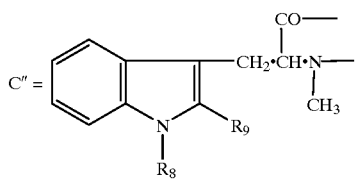

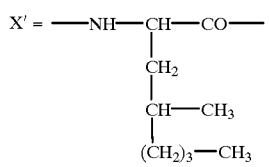

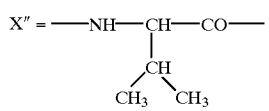

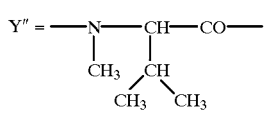

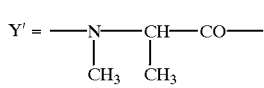

EXAMPLE 1

Characterisation of the Strain F/92-4471108 (NRRL 21123).

The fungal strain NRRL 21123 which produces compounds A and B was isolated from a leaf litter sample collected near La Plata, Argentina.

When grown on a 2% malt agar Medium A (2% malt extract, 0,4% yeast extract, 2% agar in deionised water) the strain NRRL 21123 produces after three days of incubation at 27° colonies of 25 to 35 mm diameter. Colonies usually develop a short aerial mycelium which is white to grey or greyish-brown.

Measured by colony diameters on Medium A, the optimal temperature for growth is between 21° and 30°, the minimal temperature is between 0° and 6°, and maximal temperature is between 33° and 38°. Sporulation was observed after four days incubation in a range between 21° and 33°.

The fungal strain NRRL 21123 produces hyaline to very light brown conidia on phialidic or annelidic conidiogenous cells, within well defined pycnidia. The conidia are generally five-celled, cylindrical, usually slightly curved and the majority measure 24-26×2,6-4 um. Each conidium bears at one end a single hyaline unbranched appendage and at the other terminal cell two to four (usually three) hyaline and unbranched appendages.

Based on these morphological characteristics and following the identification keys in: B. C. Sutton (1980): The Coelomycetes (published by the Commonwealth Mycological Institute, Surrey, England), the strain NRRL 21123 can be accomodated within the genus Bartalinia Tassi.

EXAMPLE 2

Fermentation

The strain NRRL 21123 is grown for 15 days at 21° on an agar slant containing Medium A (2% malt extract, 0,4% yeast extract, 2% agar, deionized water). The conidia of one slant are suspended in 10 ml sterile tap water. 1 ml conidial suspension is inoculated into each of two 500 ml Erienmeyer flasks containing 200 ml Medium B (2% malt extract, 0.4% yeast extract in deionised water). These flasks are incubated for 6 days at 21° on a rotary shaker at a speed of 200 RPM to produce the preculture. 2 ml of the preculture are then inoculated into each of 200 500 ml Erlenmeyer flasks containing 200 ml Medium C (2.2% maltose monohydrate, 0.72% yeast extract in deionized water). These flasks are incubated at 21° on a rotary shaker at a speed of 200 RPM and harvested by combining after 6 days for further workup.

EXAMPLE 3

Isolation of Metabolites, Compounds A and B 50 l fermentation broth of strain NRRL 21123, as described in Example 2, is filtered using Clarcel as a filter aid. The wet mycelium is collected and extracted 3× with 15 l methanol-acetone (1:1). The combined extracts are concentrated in a circulating evaporator in vacuo to approx. 3 l of residual aqueous solution. This is extracted 4× with 1 l of ethyl acetate. The ethyl acetate extracts are combined and concentrated in vacuo to 25 g of oily residue, which is then partitioned 3× in the solvent system 90% aqueous methanol and hexane, the lower phase giving after concentration in vacuo 4.5 g crude solid. This solid is applied to a 5.5 cm i.d.×38 cm silica gel column (Merck, Kieselgel 60, 40–63

μm) and chromatographed with 1.4 l of methyl-tert-butylether/methanol (98:2), then with 1 l (95:5). The flow rate is maintained at 110 ml/min. Fractions which show activity in an ICAM-1 expression inhibition assay as described in Example 4 (90 ml each), containing either compound A (Nos. 9–10) or compound B (Nos. 11–25) are pooled.

Compound A

Combined fractions 9–10 from the silica gel chromatography described above are evaporated to dryness in vacuo to give 1 g crude material. This is further purified by preparative HPLC, using a 50 mm i.d.×250 mm Merck column with 7 μm LiChrospher RP-18. A linear 80→100% gradient of methanol in water is applied over 60 minutes. The flow rate is 25 ml/min., 25 ml fractions are collected and monitoring is at 220 nm. Fractions 56–62 are combined, based on UV, TLC and biological activity, and then concentrated in vacuo to give 0.6 g residue. Final purification is achieved by Sephadex LH 20 chromatography with a 2.7 cm i.d.×86 cm column and with methanol elution. The elution fractions, which contain compound A in pure form, as determined by TLC, are combined and evaporated to dryness in vacuo to give 580 mg of a colorless powder. The properties of compound A are given in Table 1 below.

Compound B

Combined fractions 11–25 give, after evaporation of the solvent in vacuo, 2 g crude material, which is further purified by preparative HPLC, using a 50 mm i.d.×250 mm Merck column with 7 μm LiChrospher RP-18. Elution is performed with a linear 80→100% gradient of methanol in water over 60 minutes. The flow rate used is 25 ml/min., 25 ml fractions are collected and detection is at 220 nm. Fractions 47–55 contain the majority of compound B, based on UV, TLC and biological activity. The fractions are combined, evaporated in vacuo to yield 0.4 g residue. This is further purified with Sephadex LH 20 chromatography on a 2.7 cm×86 cm column and with methanol elution. 12 ml fractions are collected, monitoring is at 220 nm. Based on UV, TLC and biological activity, fractions 23×27 are combined, evaporated in vacuo to give 0.3 g residue. A final silica gel chromatography step using a 2.2 cm i.d.×16 cm column, filled with Merck Kieselgel 60, 40–63 μm, and with toluene-ethanol (95:5) elution yields pure compound no. B, as determined by TLC. The resultant fractions are combined and evaporated to dryness in vacuo, to give 145 mg of a colorless powder. The properties of compound B are also given in Table 1 below.

Figure 2:
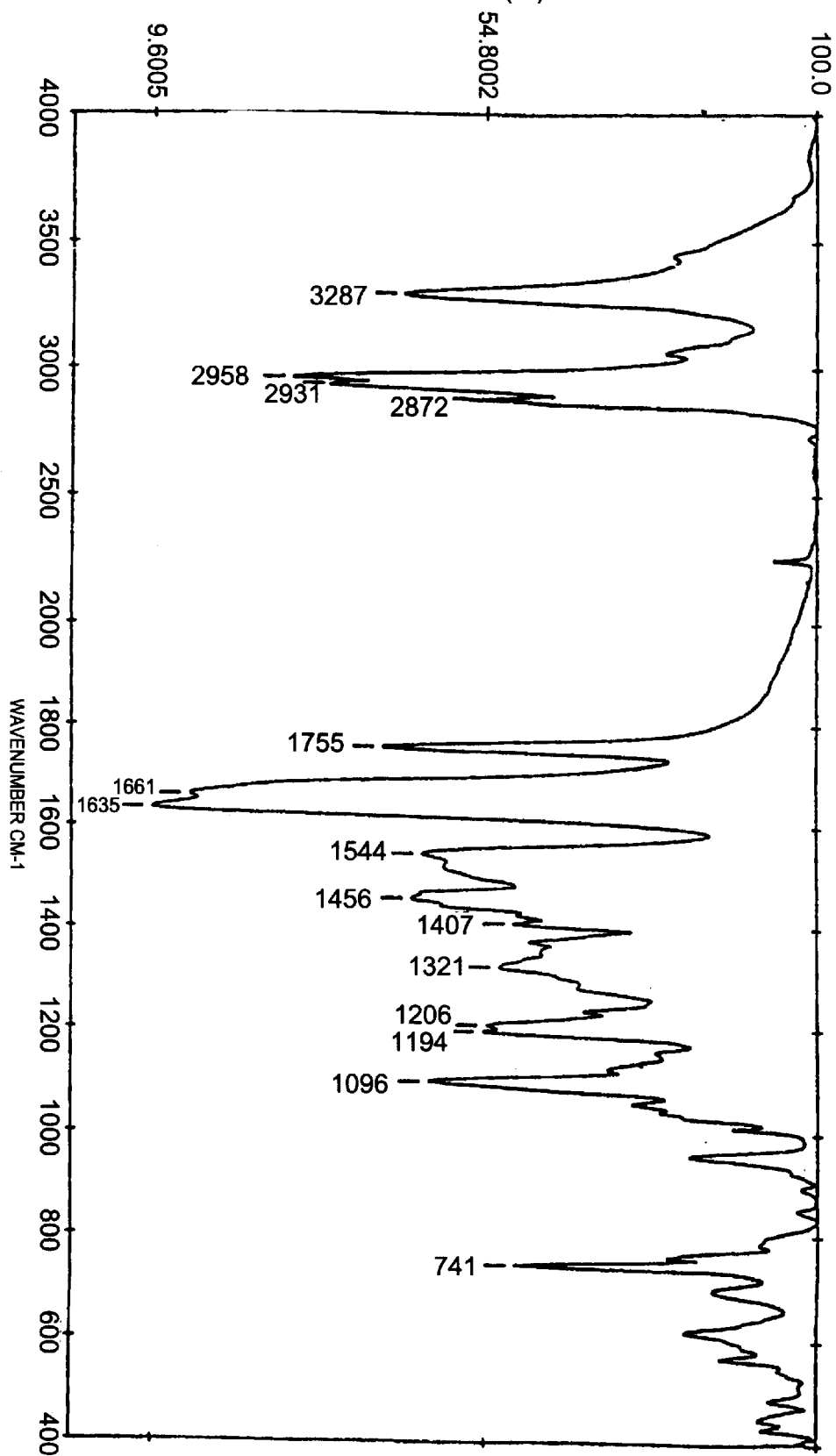
FIG. 2 shows the IR spectrum of compound A.
Figure 3:
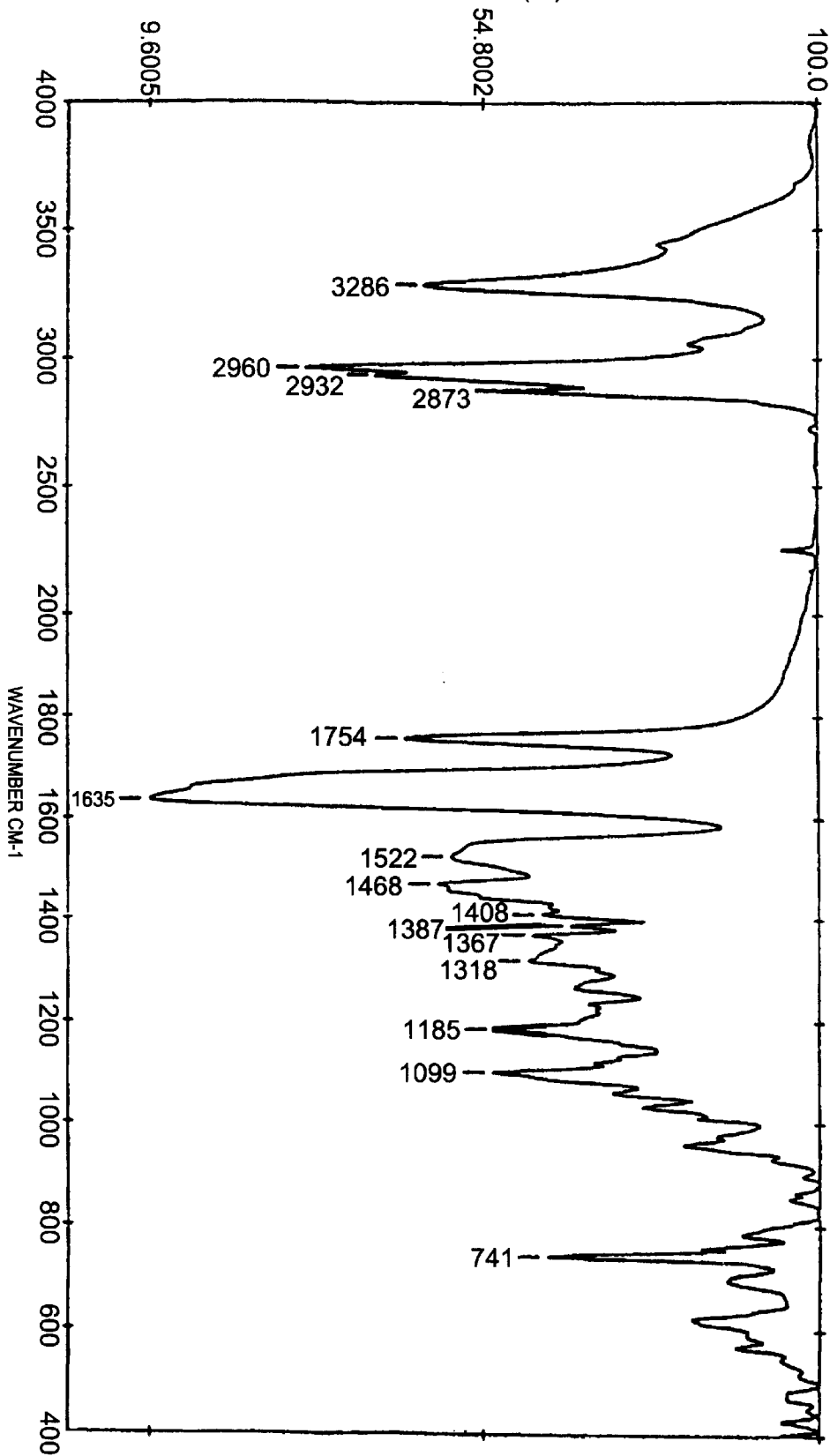
FIG. 3 shows the IR spectrum of compound B.
Figure 4:
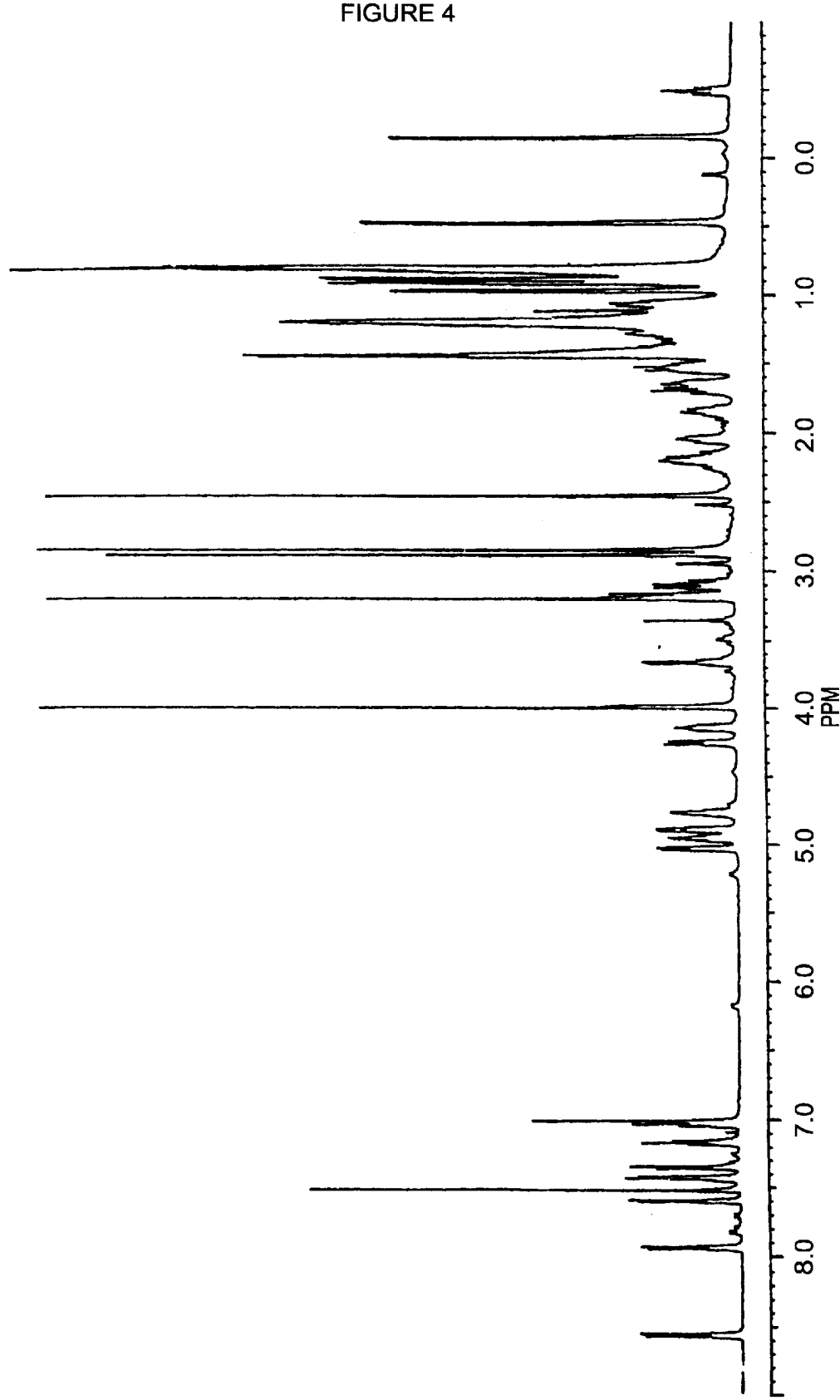
FIG. 4 shows the proton NMR spectrum of compound A.
Figure 5:
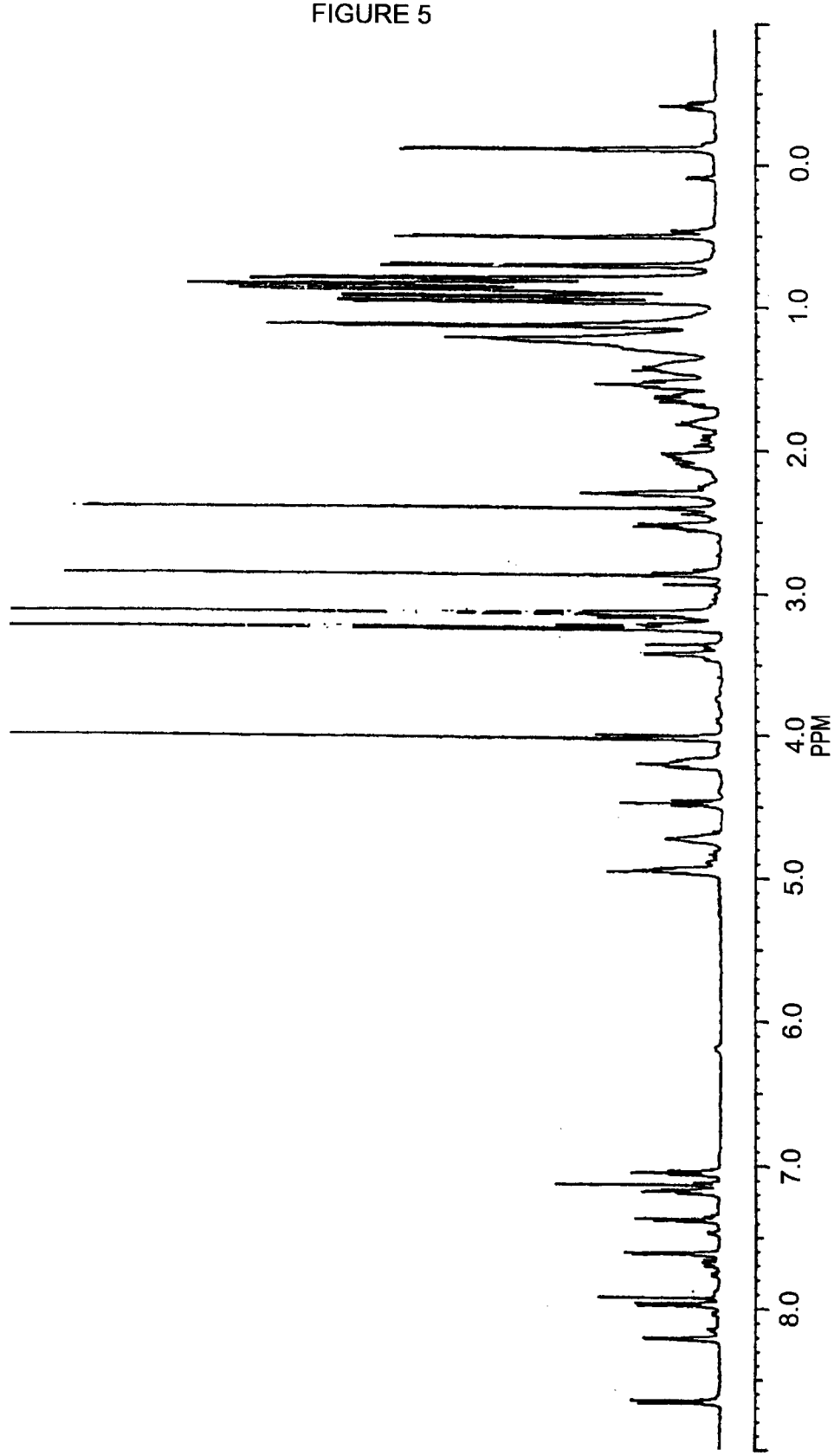
FIG. 5 shows the proton NMR spectrum of compound B.
Figure 6:
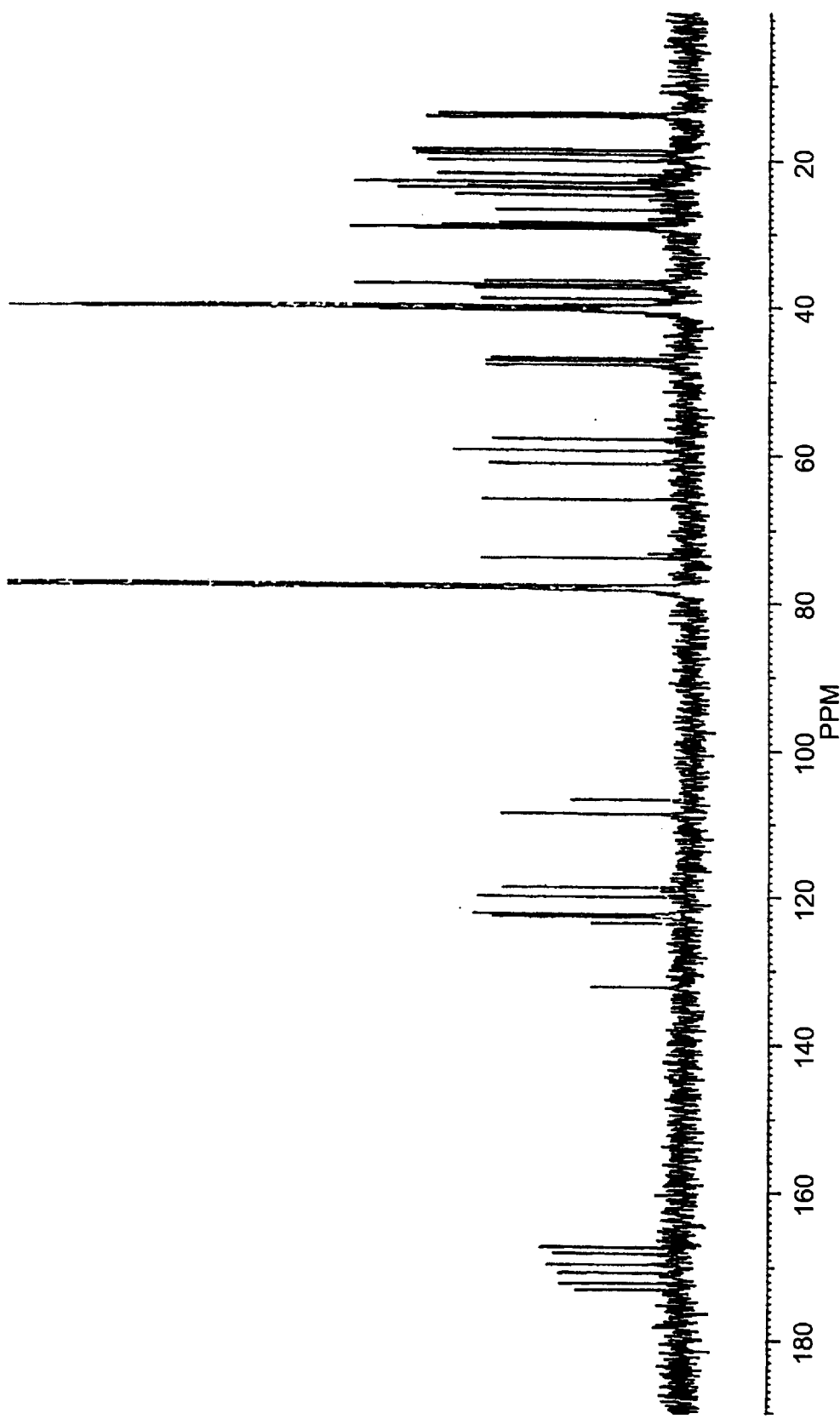
FIG. 6 shows the $^{13}C$ NMR spectrum of compound A.
Figure 7:
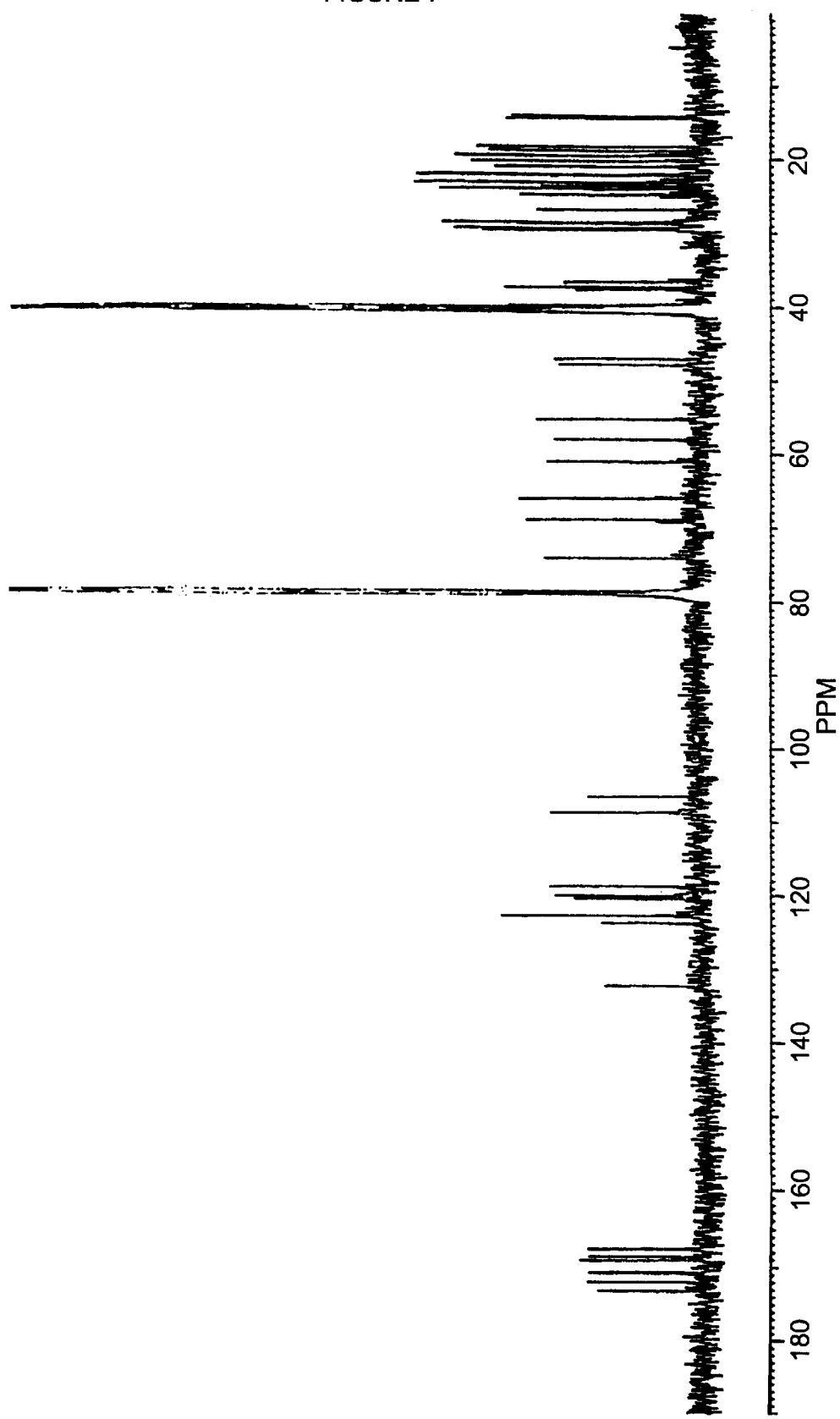
FIG. 7 shows the $^{13}C$ NMR spectrum of compound B.

Table 1 below refers to FIGS. 1 to 7.

TABLE 1

| Property | Compoumnd A | Compound B |
|---|---|---|
| 1. Appearance | colorless powder | colorless powder |
| 2. $[\alpha]_D^{25}$ | −234° (MeOH, c = 1.11) | −243° (MeOH, c = 1.08) |
| 3. Mass spectrum (FAB) | m/e = 977 (MH$^+$) | m/e = 949 (MH$^+$) |
| 4. Molecular formula | $C_{53}H_{64}N_8O_9$ | $C_{51}H_{80}N_8O_9$ |
| 5. UV spectrum (MeOH) | See FIG. 1a | See FIG. 1b |
| 6. IR spectrum (KBr) | See FIG. 2 | See FIG. 3 |
| 7. Proton NMR, 500 MHz, DMSO-d$_6$ as int. stand. | in CDCl$_3$-DMSO-d$_6$ = 3:2, see FIG. 4 | in CDCl$_3$-DMSO-d$_6$ = 4:1, see FIG. 5 |
| 8. $^{13}$C NMR, 125.7 MHz, DMSO-d$_6$ as int. stand. | in CDCl$_3$-DMSO-d$_6$ = 3:2, see FIG. 6 | in CDCl$_3$-DMSO-d$_6$ = 4:1, see FIG. 7 |

TABLE 1-continued

| Property | Compoumnd A | Compound B |
|---|---|---|
| 9. Solubility | soluble in chloroform, methanol, DMSO, insoluble in water and hexane | |
| 10. TLC$^a$ (Rf value) | 0.31 | 0.24 |
| 11. HPLC$^b$ (Rt) | 4.2 minutes | 3.3 minutes |

$^a$5 cm × 20 cm Silica gel plate 60 F$_{254}$ (Merck); toluene-MeOH (95:5)
$^b$Merck LiChrospher 100 RP-18 (5 μm), 4 × 125 mm; MeOH-H$_2$O (9:1); 1.2 ml/min.; detection at 220 nm using a Waters 996 photodiode array detector

EXAMPLE 4

Compound of Formula I
(A=A', R$_6$=COOCH$_3$, B=B', R$_1$=CH$_3$, C=C', R$_8$=OCH$_3$, ----=db, X=X', Y=Y')

A cold solution of HCl in ether (30 ml, 17% w/v, −20°) is added to a mixture of 2 g of compound A and 1.65 ml of methanol and is kept at −20° for 3 days. The reaction mixture is then poured onto aqueous bicarbonate solution and extracted with ethyl acetate. The organic extract is dried over sodium sulfate, filtered and evaporated in vacuo. The crude product is dissolved in 30 ml of methanol/conc. aqueous HCl (9/1) and stirred at room temperature for 3 h. The solution is then diluted with water and extracted with ethyl acetate. The organic extract is dried over sodium sulfate, filtered and evaporated in vacuo. The crude reaction mixture is purified by reversed phase chromatography on LiChroprep RP-8 (gradient: methanol/water=8/2 to 10/0) and subsequent chromatography on silica gel (gradient toluene/methanol=100/0 to 95/5) to yield the title substance as a colorless foam and the open-chain derivative of formula IV (R$_6$=COOCH$_3$, R$_7$=CH$_3$) as a colourless solid.

TLC: silica gel, toluene/methanol=9/1, Rf=0.41 (title substance), Rf=0.38 (open-chain derivative); reversed phase RP-8, methanol/water/trifluoro acetic acid=95/4/1, Rf=0.34 (title substance), Rf=0.51 (open-chain derivative).

EXAMPLE 5

Compound of Formula I
(A=A', R$_6$=COOH, B=B', R$_1$=CH$_3$, C=C', R$_8$=OCH$_3$, ----=db, X=X', Y=Y')

A solution of 209 mg of the compound of formula I of example 4 in 15 ml of t-butanol/conc. aqueous HCl (9/1) is heated to 60° for 8 h. The reaction mixture is poured onto saturated aqueous bicarbonate solution end extracted with ethyl acetate. The organic phase is washed with pH 7 buffer, dried over sodium sulfate and evaporated in vacuo. The crude product is purified by chromatography on silica gel (gradient: toluene/methanol=100/0 to 95/5) to yield the title substance as a colorless foam. TLC: silica gel, toluene/methanol=9/1, Rf=0.25; reversed phase RP-8, methanol/water=92/8, Rf=0.34.

EXAMPLE 6

Compound of Formula I
(A=A', R$_6$=CO.NH.CH$_3$, B=B', R$_1$=CH$_3$, C=C', R$_8$=OCH$_3$, ----=db, X=X', Y=Y')

A solution of 10 mg of the compound of example 5 in 0.5 ml of dichloromethane is cooled to 0° and 50 μl of thionyl chloride are added. The reaction mixture is kept at 0° for 1.5 h and then evaporated at 0° in vacuo. The remaining yellow oil is dissolved in 1 ml of dichloromethane at 0° and 100 μl of a 40% aqueous methylamine solution are added. After 45 min the reaction mixture is poured onto 0.1 M aqueous HCl, extracted with ethyl acetate and partitioned between ethyl acetate and sat. aqueous bicarbonate solution. The organic phase is washed with brine, dried over sodium sulfate and evaporated in vacuo. The crude product is purified by chromatography on silica gel (gradient: toluene/ethyl acetate/methanol=100/0/0 to 65/25/10) to yield the title substance as a colorless foam.

TLC: silica gel, toluene/methanol=9/1, Rf=0.25; reversed phase RP-8, methanol/water=95/5, Rf=0.33.

Analogously as described in example 6 the following compounds of formula I (A=A', B=B', C=C', X=X', Y=Y' and $R_1$=$CH_3$) are obtained:

| Ex: | $R_6$ | $R_8$ | ----- |
|---|---|---|---|
| 7 | —CO—N(morpholine) | $OCH_3$ | db |
| 8 | —CO—N($CH_3$)($CH_3$) | " | db |
| 9 | —CO—N(aziridine) | " | db |
| 10 | —CO—N(pyrrolidine) | " | db |
| 11 | —CO—N(piperidine) | " | db |
| 12 | —CO—N(($CH_2)_2$·$CH_3$)($CH_3$) | " | db |

EXAMPLE 13

Compound of Formula I (A=A', $R_6$=COO.iPr, B=B', $R_1$=$CH_3$, C=C', $R_8$=$OCH_3$, ----=db, X=X', Y=Y')

A solution of 15 mg of the compound of example 5 in 0.75 ml of dichloromethane is cooled to 0° and 75 µl of thionyl chloride are added. The reaction mixture is kept at 0 for 2 h and then evaporated at 0° in vacuo. The remaining yellow oil is dissolved in 1 ml of dichloromethane at 0° and 30 µl of i-propanol are added. After 3 h at 0° the reaction mixture is poured onto 0.1 M aqueous HCl, extracted with ethyl acetate. The organic phase is washed with brine, dried over sodium sulfate and evaporated in vacuo The crude product is purified by chromatography on silica gel (gradient: toluene/methanol=100/0 to 95/5) to yield the title substance as a colorless foam. TLC: silica gel, toluene/methanol=9/1, Rf=0.47; reversed phase RP-8, methanol/water=95/5, Rf=0.37.

Analogously as described in example 9 the following compounds of formula I (A=A', B=B', C=C', X=X', Y=Y' and $R_1$=$CH_3$) are obtained:

| Ex. | $R_6$ | $R_8$ | ===== |
|---|---|---|---|
| 14 | —COO.$C_2H_5$ | $OCH_3$ | db |
| 15 | —COO.nPr | -"- | db |

EXAMPLE 16

Compound of Formula I (A=A', $R_6$=$COCH_3$, B=B', $R_1$=$CH_3$, C=C', $R_8$=$OCH_3$, ----=db, X=X', Y=Y')

A solution of 200 mg of the compound A in 2 ml is added to a methyl Grignard solution of 2 mmol in 5 ml of ether and stirred at room temperature for 24 h. Then additional 2 mmol of MeMgJ in ether are added and again stirred for 24 h at room temperature. The reaction mixture is poured onto 0.1 M HCl solution end extracted with ethyl acetate. The organic phase is washed with sodium bicarbonate solution and brine, dried over sodium sulfate and evaporated in vacuo. The crude reaction mixture is purified by chromatography on silica gel (gradient: toluene/ethyl acetate/methanol=100/0/0 to 68/27/5) to yield the title substance as well as considerable amounts of unchanged starting material. TLC: silica gel, toluene/methanol=9/1, Rf=0.30.

EXAMPLE 17

Compound of Formula I (A=A', $R_6$=$CH_2OH$, B=B', $R_1$=$CH_3$, C=C', $R_8$=$OCH_3$, ----=db, X=X', Y=Y')

0.5 ml of a 2 M solution of borane dimethylsulfide complex are added to a solution of 27 mg of the compound of example 5 in 2 ml of tetrahydrofuran at room temperature. The reaction mixture is stirred for 2.5 h, poured onto 0.1 M HCl and extracted with ethyl acetate. The organic phase is washed with phosphate buffer (pH 7), dried over sodium sulfate and evaporated in vacuo. The crude material is purified by silica gel chromatography (gradient: toluene/methanol=100/0 to 95/5) to yield the title substance as a colorless foam. TLC: silica gel, toluene/methanol=9/1, Rf=0.27; reversed phase RP-8, methanol/water=92/8 no separation from starting material.

EXAMPLE 18

Compound of Formula I (A=A', $R_6$=CN, B=B', $R_1$=$CH_3$, C=C', $R_8$=H, ----=db, X=X', Y=Y')

18 mg of Palladium on activated carbon (10%) are added to a solution of 53 mg of the compound A and 66 mg of sodium acetate in 4 ml of acetic anhydride. The reaction mixture is stirred at room temperature under an hydrogen atmosphere for 20 h (50% conversion by TLC) and then poured onto aqueous sodium bicarbonate solution and extracted with ethyl acetate. The organic solution is dried over sodium sulfate and evaporated in high vacuum. The crude product is purified by reversed phase chromatography on RP-8 material (gradient: methanol/water=80/20 to 100/0) to yield the title substance as a colorless foam. TLC: silica gel, toluene/methanol=9/1, Rf=0.33; reversed phase RP-8, methanol/water=92/8, Rf=0.50 (starting material Rf=0.44).

EXAMPLE 19

Compound of Formula I
(A=A', $R_6$=CHO, B=B', $R_1$=$CH_3$, C=C', $R_8$=$OCH_3$, ----=db, X=X', Y=Y')

35 mg of Dess-Martin periodinane reagent (1,1,1-tris(acetyloxy)-1,1-dihydro-1,2-benziodoxol-3(1H)-one) are added to a solution of 50 mg of the compound of example 17 in 4 ml of dichloromethane and the suspension is stirred at 20° for 3 hours. Then the crude reaction mixture is poured onto silica gel and eluted with ethyl acetate. The product containing fractions are combined, evaporated in vacuo and purified by chromatography on silica gel (gradient toluene/methanol=100/0 to 95/5) to yield the title substance as a colorless foam.

EXAMPLE 20

Compound of Formula I
(A=A', $R_6$=CH=$CH_2$, B=B', $R_1$=$CH_3$, C=C', $R_8$=$OCH_3$, ----=db, X=X', Y=Y')

A solution of methyl-Wittig reagent, prepared by stirring a mixture of methyltriphenylphosphonium bromide and sodium amide in dry THF, is slowly added at 200 to a solution of 24.7 mg of the compound of example 19 in dry THF until the yellow color of the reagent remains. Then the reaction mixture is poured onto 0.1 M hydrochloric acid and extracted with ethyl acetate. The organic extract is evaporated in vacuo and the remaining crude product is purified by silica gel chromatography (gradient toluene/methanol=100/0 to 97/3) to yield the title compound as a colorless foam.

EXAMPLE 21

Compound of Formula I
(A=A', $R_6$=CH=CH—$C_2H_5$, B=B', $R_1$=$CH_3$, C=C', $R_8$=$OCH_3$, ----=db, X=X',=Y')

The title compound is prepared analogously as described in example 20. TLC: silica gel, toluene/methanol=9/1, Rf=0.44.

EXAMPLE 22

Compound of Formula I
(A=A', $R_6$=$CH_2N_3$, B=B', $R_1$=$CH_3$, C=C', $R_8$=$OCH_3$, ----=db, X=X', Y=Y')

To a solution of 30 mg of the compound of example 17 and 12 mg of triphenylphosphine in 3 ml of dry THF 150 µl of a 0.38 M toluene solution of hydrazoic acid are added. Diethyl azodicarboxylate is added at room temperature until the solution remains yellow and the mixture is stirred at room temperature for 10 min. The crude reaction mixture is poured onto 5 g of aluminium oxide (neutral) and eluted with ethyl acetate. The product containing fractions are evaporated in vacuo and purified by chromatography on silica gel (gradient: toluene/methanol=99.5/0.5 to 95/5) to yield the title substance as a colorless foam. TLC: silica gel, toluene/methanol=9/1, Rf=0.46; reversed phase RP-8, methanol/water/ TFA=95/4/1, Rf=0.41.

EXAMPLE 23

Compound of Formula I
(A=A', $R_6$=$CH_2$.$NH_2$, B=B', $R_1$=$CH_3$, C=C', $R_8$=$OCH_3$, ----=db, X=X', Y=Y')

A solution of 20 mg of the compound of example 22 in 2 ml of methanol is stirred in an hydrogen atmosphere at 4° with 4 mg of palladium on charcoal (10%) for 20 hours. The catalyst is filtered off and the reaction mixture is evaporated in vacuo. The crude product is purified by reversed phase chromatography on RP-8 (gradient: methanol/water 0.5% TFA=80/20 to 100/0) to yield the title compound as a colorless foam.

TLC: reversed phase RP-8, methanol/water/TFA=95/4/1, Rf=0.69.

EXAMPLE 24

Compound of Formula I
(A=A', $R_6$=CH=$CBr_2$, B=B', $R_1$=$CH_3$, C=C', $R_8$=$OCH_3$, ----=db, X=X', Y=Y')

A solution of 225 mg of the compound of example 19 in 2.5 ml of dichloromethane is added to a mixture of 30 mg of zinc powder, 120 mg of triphenylphosphine and 150 mg of tetrabromomethane and is stirred for 30 min at room temperature. The mixture is then poured onto 5 g of aluminium oxide and eluted with ethyl acetate. The product containing fractions are evaporated in vacuo and purified by chromatography on silica gel (gradient: toluene/methanol=99.5/0.5 to 97/3) to yield the title substance as a colorless solid foam. TLC: silica gel, toluene/methanol=9/1, Rf=0.27.

EXAMPLE 25

Compound of Formula I
(A=A', $R_6$=C≡CH, B=B', $R_1$=$CH_3$, C=C', $R_8$=$OCH_3$, ----=db, X=X', Y=Y')

A solution of n-butyl lithium in hexane (3 molequivalents) is added to 50 mg of the compound of example 24 at −78° during 2 hours. The reaction mixture is poured onto 0.1 M of aqueous HCl and extracted with ethyl acetate. The organic phase is washed with bicarbonate solution and brine and is evaporated in vacuo. The crude product is purified by chromatography on silica gel (gradient: toluene/methanol=99.510.5 to 97/3) to yield the title substance as a colorless solid foam. TLC: silica gel, toluene/methanol=9/1, Rf=0.44.

EXAMPLE 26

Compound of Formula I
(A=A', $R_6$=CH=CH—CN, B=B', $R_1$=$CH_3$, C=C', $R_8$=$OCH_3$, ----=db, X=X', Y=Y')

A solution of 30 mg of the compound of example 19 and 270 mg of cyanomethylene-triphenylphosphorane in 5 ml of toluene is stirred at room temperature for 4 h. Then the crude reaction mixture is filtered over aluminium oxide (neutral) and eluted with ethyl acetate. The product containing fractions are combined and evaporated in vacuo. The title substance is a mixture of E/Z isomers. TLC: silica gel, toluene/methanol=9/1, Rf=0.39.

EXAMPLE 27

Compound of Formula I
(A=A', $R_6$=$CH_2$Cl, B=B', $R_1$=$CH_3$, C=C', $R_8$=$OCH_3$, ----=db, X=X', Y=Y')

A solution of 20 mg of the compound of example 17 in 1 ml of toluene is added to a solution of 10 mg of dichlorotriphenyl phosphorane in 1 ml of toluene and stirred at 60°. After 2 h additional 35 mg of dichlorotriphenyl phosphine are added. After 1 h the reaction mixture is filtered over neutral aluminium oxide and is eluted with ethyl acetate. The product containing fractions are evaporated and the crude material is purified by chromatography on silica gel (gradient: toluene/methanol=100/0 to 97/3) to yield the title substance as a colorless solid foam. TLC: silica gel, toluene/methanol=9/1, Rf=0.39.

EXAMPLE 28

Compound of Formula I
(A=A', $R_6$=$CH_2$.O.$CH_3$, B=B', $R_1$=$CH_3$, C=C', $R_8$=$OCH_3$, ----=db, X=X', Y=Y')

A solution of 34 mg of the compound of example 17 in 6 ml of dichloromethane and 100 mg of silica gel is treated with an etheral diazomethane solution until the starting material is consumed. To ged rid of the polymethylene formed during the course of the reaction, the mixture is filtered, evaporated and fresh dichloromethane and silica gel are added. After final evaporation in vacuo, the crude material is purified by chromatography on silica gel (gradient: toluene/methanol=99.7/0.3 to 97/3) to yield the title substance as a colorless solid foam. TLC: silica gel, toluene/methanol=9/1, Rf=0.34.

EXAMPLE 29

Compound of Formula I
(A=A', $R_6$=

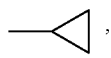,

B=B', $R_1$=$CH_3$, C=C', $R_8$=$OCH_3$, ----=db, X=X', Y=Y')

A solution of 13 mg of the compound of example 20 and 2.8 mg of palladium acetate in 2.5 ml of dichloromethane is treated with an etheral solution of diazomethane at room temperature until the starting material is consumed. The crude reaction mixture is filtered over silica gel and eluted with toluene/methanol. The product containing fraction is evaporated and the crude material is purified by chromatography on silica gel (gradient: toluene/methanol=99.5/0.5 to 97/3) to yield the title substance as a colorless solid foam.
TLC. silica gel, toluene/methanol=9/1, Rf=0.38; reversed phase RP-8, methanol/phosphate buffer pH7=92/8, Rf=0.27.

EXAMPLE 30

Compound of Formula I
(A=A', $R_6$=COO.CH($C_6H_5$)$_2$, B=B', $R_1$=$CH_3$, C=C', $R_8$=$OCH_3$, ----=db, X=X', Y=Y')

A solution of 8.2 mg of the compound of example 5 and 3.1 mg of diphenyidiazomethane in 0.5 ml of toluene is heated to 60° for 3 hours. The solution is then directly applied to column chromatography on silica gel (gradient: toluene/methanol=100/0 to 97/3) to yield the title substance as colorless solid foam. TLC: silica gel, toluene/methanol=9/1, Rf=0.46.

EXAMPLE 31

Compound of Formula I
(A=A', $R_6$=

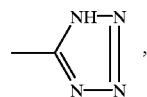,

B=B', $R_1$=$CH_3$, C=C', $R_8$=$OCH_3$, ----=db, X=X', Y=Y')

A solution of 50 mg of the compound A in 1 ml of dimethylformamide is heated with 125 mg of tributyltin chloride and 25 mg of sodium azide to 100° for 8 days. The mixture is then poured onto 1 M aqueous HCl, extracted with ethyl acetate. The organic phase is washed with brine, dried over sodium sulfate and evaporated in vacuo. The crude product is purified by chromatography on silica gel (gradient: toluene/methanol=100/0.25 to 100/2.5) to yield the title substance as a colorless foam.

TLC: silica gel, toluene/methanol=9/1, Rf=0.12; reversed phase RP-8, methanol/phosphate buffer pH7=92/8, Rf=0.48.

EXAMPLE 32

Compound of Formula I
(A=A', $R_6$=CN, B=B', C=C', $R_8$=$CH_3$, ----=db, X=X', Y=Y')

A solution of 20 mg of the compound of example 18 in 1 ml of dry dimethylformamide is mixed with 1 ml of iodomethane and a solution of 5 mg of sodium bis (trimethylsilyl)amide in 0.3 ml of dimethylformamide is added. After stirring of the reaction mixture for 1.5 h at room temperature, the mixture is poured onto 0.1 M aqueous HCl, extracted with ethyl acetate and partitioned between ethyl acetate and saturated aqueous bicarbonate solution. The organic phase is washed with brine, dried over sodium sulfate and evaporated in vacuo. The crude product is purified by chromatography on silica gel (gradient: toluene/methanol=100/0.25 to 100/2.5) to yield the title substance as a colorless foam. TLC: silica gel, toluene/methanol=9/1, Rf=0.43.

Analogously as described in example 32 the following compounds of formula I are obtained (A=A', $R_6$=CN, B=B', X=X', Y=Y'):

| Example | C | $R_8$ | ==== |
|---------|-----|----------|----|
| 33 | C' | $C_2H_5$ | db |
| 34 | C' | Bz | db |

EXAMPLE 35

Compound of Formula I
(A=A', $R_6$=CN, B=B', C=C', $R_8$=$CH_2C(CH_3)_3$, ----=db, X=X', Y=Y')

To a solution of 38 mg of the compound of example 38 in 2 ml of acetic acid and 0.2 ml of pivalaldehyde, 30 μl of a 2 M borane-dimethylsulfide complex solution in THF is added and the mixture is stirred 5 min at room temperature. The mixture is then poured onto sodium bicarbonate/ethyl acetate and a small amount of water is added. The organic layer is separated, washed with brine, dried over sodium sulfate and evaporated in vacuo. The residual colorless oil (TLC: silica gel, toluene/methanol 9/1, Rf=0.53) is dissolved in 3 ml of THF and a THF solution of 2,3-dichloro-5,6-dicyano-1,4-benzoquinone (DDQ, 8 mg in 0.2 ml) is added at RT until the reaction mixture turned dark. The mixture is filtered over 5 g of silica gel and eluted with toluene/methanol=100/0.5 to 95/5) to yield the title substance as a colorless foam. TLC: silica gel, toluene/methanol 9/1, Rf=0.49.

Analogously as described in example 35 the following compounds of formula I are obtained (A=A', $R_6$=CN, B=B', X=X', Y=Y'):

| Example | C | $R_8$ | === |
|---------|---|-------|-----|
| 36 | C' | Bz | sb |
| 37 | C' | CH(CH$_3$)$_2$ | db |

EXAMPLE 38

Compound of Formula I
(A=A', $R_6$=CN, B=B', C=C', $R_8$=H, ----=sb, X=X', Y=Y')

A heterogenous mixture of 25 mg of the compound of example 18, 1 ml of trifluoroacetic acid and 0.3 ml of triethylsilane is vigorously stirred under argon atmosphere at 4° for 20 h. The reaction mixture is poured onto saturated aqueous bicarbonate solution and extracted with ethyl acetate. The organic phase is washed with brine, dried over sodium sulfate and evaporated in vacuo. The crude product is purified by chromatography on silica gel (gradient: toluene/methanol=100/0.5 to 100/5) to yield the title substances as a colorless foams. TLC: silica gel, toluene/methanol=9/1, indoline A Rf=0.16, indoline B Rf=0.10; reversed phase RP-8, methanol/water/TFA=95/4/1, indoline A+B Rf=0.71.

EXAMPLE 39

Compound of Formula I
(A=A', $R_6$=CN, B=B', C=C', $R_8$=O.(CH$_2$)$_2$.CH$_3$, ----=db, X=X', Y=Y')

To a solution of 30 mg of the compound of example 38 (mixture of diastereoisomers) in 1 ml of methanol 100 mg of sodium tungstate (Na$_2$WO$_4$.2H$_2$O) and 100 µl of a 30% hydrogen peroxide solution are added. The reaction mixture is stirred at room temperature for 20 min and then directly purified via gel-permeation chromatography (Sephadex LH-20, methanol/ethyl acetate=1:1). The fractions containing the N-hydroxy indole intermediate are evaporated, the residue is taken up in 2 ml of dry DMF, 2 ml of propyl iodide and 7.5 mg of sodium bis(trimethylsilyl)amide are added. After stirring 30 min at room temperature the reaction mixture is poured onto 0.1 M of hydrochloric acid and extracted with ethyl acetate. The organic layer is washed with sodium bicarbonate solution and brine and is evaporated in vacuo. The product is purified by chromatography on silica gel (gradient: toluene/methanol=100/0.5 to 98/2) and reversed-phase chromatography (RP-8, gradient aqueous methanol=75 to 100%) to yield the title substance as a colorless foam. TLC: silica gel, toluene/methanol=90/10, Rf=0.51, RP-8, methanol/phosphate buffer pH7=92/8, Rf=0.30.

EXAMPLE 40

Compound of Formula I
(A=A', $R_6$=CN, B=B', C=C', $R_8$=O.C$_2$H$_5$, ----=db, X=X', Y=Y')

The title compound is prepared analogously as described in example 39.

EXAMPLE 41

Compound of Formula I
(A=A', $R_6$=CN, B=B', C=C", $R_8$=OCH$_3$, $R_9$=Br, ----=db, X=X', Y=Y')

A solution of 50 mg of the compound A in 2 ml of tetrachloromethane is stirred with 3 mg of iron powder and a solution of 10 mg of bromine in tetrachloromethane is added during 1 hour. The crude reaction mixture is poured onto aqueous bicarbonate solution and extracted with ethyl acetate. The organic phase is washed with sodium thiosulfate solution and brine and is evaporated in vacuo. The crude product is purified by chromatography on silica gel (gradient: toluene/methanol=99.5/0.5 to 97/3) to yield the title substance as a colorless solid foam. TLC: silica gel, toluene/methanol=9/1, Rf=0.48; reversed phase RP-8, methanol/water=92/8, Rf=0.19.

EXAMPLE 42

Compound of Formula I
(A=A', $R_6$=CSNH$_2$, B=B', $R_1$=CH$_3$, C=C', $R_8$=OCH$_3$, ----=db, X=X', Y=Y')

A solution of 50 mg of compound A and 50 mg of diphenylphosphinodithioic acid in 4 ml of iso-propanol is heated to 60° for 3 days. The reaction mixture is cooled to −20°, the precipitate is removed by filtration, the solution is diluted with ethyl acetate and extracted with aqueous sodium bicarbonate solution. The organic phase is evaporated in vacuo and the crude product purified by chromatography on silica gel (gradient: toluene/methanol=100/0.5 to 96/4) to yield the title substance as a colorless foam.
TLC: silica gel, toluene/methanol=9/1, Rf=0.29.

Biological Activity

The activities of the compounds of the invention are tested in assays for cytotoxicity and inhibition of ICAM-1, VCAM-1 and E-selectin expression, as well as cell proliferation. The concentrations of compound required for half-maximal inhibition (IC$_{50}$) in each assay are given in Table 2 below.

TABLE 2

| | IC$_{50}$ (µM)/Assay | | | | | |
|---|---|---|---|---|---|---|
| Compound | ICAM-1 (HaCat) | ICAM-1 (HMEC) | VCAM-1 (HMEC) | E-selectin (HUVEC) | cytotox (24 hr.) | cell prolif. (HaCat 72 hr) |
| compound A | 0.009 | 0.06 | 0.002 | 0.04 | >40 | 0.006 |
| compound B | 0.02 | 1.3 | 0.03 | | >40 | 0.05 |

The assays were carried out as follows:

HaCaT cells, a spontaneously-transformed, non-tumorigenic human keratinocyte cell line with highly preserved phenotypic differentiation characteristics of normal keratinocytes (Boukamp et al., 1988 J. Cell Biol. 106, 761–771), are used both for the cell proliferation assay and the ICAM-1 cell Elisa.

A. ICAM-1 CELL-ELISA ASSAY

I. Keratinocyte ICAM-1 Cell Elisa

The ICAM-1 cell Elisa used to determine inhibition of ICAM-1 expression is substantially as described by Winiski and Foster (1992, J. Invest. Dermatol., 99, 48–52). HaCaT cells are seeded in 96 well microtiter plates ($2\times10^4$ cells/well in culture medium: DMEM with 5% FCS, 100 U/ml Penicillin, 100 μg/ml Streptomycin, 2 mM Glutamine, 1 mM Na Pyruvate), grown to confluency, and then incubated in fresh test medium (as for culture medium but with 0.5% FCS instead of 5%) with or without IFN-γ/TNF-α stimulation medium (test medium+1000 U/ml IFN-γ/3 ng/ml TNF-α) both in the presence and absence of compound A or compound B for ca. 24 hrs. The medium is then washed away and the cell monolayers are fixed with 1% parafomraldehyde. The monolayers are incubated with saturating amounts of primary (mouse anti-ICAM-1 monoclonal) and secondary (goat anti-mouse peroxidase conjugated) antibodies. The subsequent peroxidase reaction uses 3-amino-9-ethylcarbazole (AEC) as substrate and generates an insoluble, colored product, which is easily measured in a standard microtiter plate reader.

II. Measure of Cytotoxicity

After the AEC reaction to detect ICAM-1 is completed, the HaCaT monolayers, are rinsed with PBS (200 μL), the PBS is poured off from the plates which are then patted dry on top of a paper towel to remove excess liquid. The bottom surfaces of the microtitre plates are gently wiped with a moist facial tissue and then again with a dry facial tissue and absorbance read at 492 nm. Before the monolayers can dry out 0.1 ml of 0.1% crystal violet solution in PBS (passed first through a 0.2 μm filter) is added to each well. The plates are then incubated at room temperature for 10 minutes, washed thoroughly 5× with PBS, excess fluid removed as described above and their absorbance read again at 492 nm before the monolayers are able to dry out. Subtraction of optical densities before and after staining gives values due to crystal violet staining and is hence related to the amounts of cell monolayer present in the wells. These values are used to correct the AEC values.

B. Endothelial cell VCAM-1, ICAM-1 and E-selectin Cell-Elisa Assay

The assay is based on a 96-well cell Elisa method using the human microvascular endothelial cell line HMEC-1 and human umbilical vein endothelial cells (HUVEC). Cells are pretreated for four hours with test compound A or compound B, stimulated for the next 8–16 hours with TNFα, then parafomaldehyde-fixed for subsequent evaluation of VCAM-1, ICAM-1 or E-selectin expression by an indirect immunoperoxidase staining technique. Cytotoxic effects are determined by counting the relative number of cells (Giemsa nuclear stain) after exposure to the test substances, in comparison to the control wells (solvent and media only). Compounds are scored positive if they exhibit $\geq$50% VCAM-1, ICAM-1 or E-selectin inhibition with <25% cell loss.

Methodology

I. Cell line: The VCAM-1 and ICAM-1 assay utilizes an immortalized (SV-40 virus large T antigen) human microvascular endothelial cell line (HMEC-1; Ades et al., Jrl Invest Dermatol 99: 683–690, 1992). HMEC-1 cells constitutively express low levels of ICAM-1 which are upregulated by inflammatory mediators. However, they only express VCAM-1 following cytokine stimulation. Dose-response and time-course experiments were performed to determine the optimal conditions for inducing VCAM-1 and ICAM-1 expression.

II. Growth conditions: HMEC-1 cells are grown in T-75 flasks (Nunc) under standard conditions (37° C., 5% CO2) with $1.5\times10^6$ cells/ml culture medium (CM=Endothelial Cell Basal Medium [EBM; Clonetics] supplemented with 10% FCS, 10 ng/ml human EGF (Boehringer), 1 μg/ml hydrocortisone (Sigma #0888), 2.2 g/l $NaHCO_3$, 15 mM Hepes, 0.11 g/l sodium pyruvate, 4 mM glutamine, 100 U/ml penicillin and 100 μg/ml streptomycin). After mild trypsinization (0.25% trypsin+0.1% EDTA for 8 min) and resuspension, the cells are reseeded every 2–3 days at a 1:3 splitting ratio.

III. VCAM-1 and ICAM-1 Cell-Elisa 96 well flat-bottom microtiter plates are precoated with bovine fibronectin (FN; Sigma #F1141) and then seeded with $2\times10^4$ cells/well in 200 μl of EBM growth medium and incubated overnight. The following day the culture medium (CM) is initially replaced with 200 μl/well of EBM assay medium (CM supplemented with 5% FCS instead of 10%) and subsequently replaced with 180 μl of medium containing either (1) appropriate concentrations of compound A or compound B, (2) corresponding concentrations of solvent/methanol-extracted medium, or (3) EBM assay medium alone and incubated for 4 hr at 37° C. Each 96-well assay is performed with duplicate wells. The cells are then stimulated by adding 20 μl of concentrated cytokine solution (2000 U/ml TNFα) and incubated for 16 hr at 37° C.

The cell monolayer is then washed with 1% paraformaldehyde in EBM medium, fixed in 2% parafomaldehyde for 15 min at room temperature (RT) and rinsed several times with PBS. The PBS is removed from the cells, and the monolayer is incubated for 30 min in PBS containing 10% normal goat serum (NGS). The NGS solution is replaced with 100 μl/well of the anti-VCAM-1 or ICAM-1 monoclonal antibody and incubated overnight at 4° C. The mAb solution is then removed and the cells rinsed several times with PBS, followed by incubation with PBS containing 10% NGS for 30–60 min at RT. The NGS solution is removed and 100 μl of horseradish peroxidase-conjugated goat $F(Ab')_2$ anti-mouse IgG antibody (Tago; 1:500 dilution in PBS containing 5% NGS) is added and the plates incubated for 1 hr at RT. The secondary antibody is then removed and the cells rinsed in PBS, which is then replaced with 150 μl/well of a freshly-prepared and filtered AEC solution (3-amino-9ethyl-carbazole; Sigma) and the plates incubated for 45–60 min at RT. The peroxidase substrate is removed and the cells rinsed in PBS. AEC absorbance values are read on a microtiter plate reader at 550 nm and corrected for "blank" or reference values at 690 nm.

IV. E-selectin assay: The E-selectin assay is performed using freshly isolated HUVEC, essentially as described for the VCAM-1 or ICAM-1 assay except for a shorter TNFα-stimulation (6–8 hours).

V. Measure of Cytotoxicity (Cell loss based on nuclear stain):

The endothelial cells are destained by replacing the PBS with 95% ethanol for 20 min (two 10 min changes) with control by microscopic evaluation. The cells are then rinsed in distilled water (Aquadest) and the monolayer covered with a 33% Giemsa solution in Aquadest for 5 min at RT. The wells are then washed with Aquadest and air dry for at least 15 min. Microscopic evaluation is used to check that only the nuclei are stained, with essentailly no cytoplasmic staining. Giemsa absorbance values are read on a microtiter plate reader at 550 nm and corrected for "blank" values (rows without cells) at 690 nm.

VI. Data Evaluation: The AEC values for constitutive VCAM-1 or E-selectin expression (unstimulated control wells) are essentially equal to those of an isotype-matched control mAb and represent the background stain. In every 96-well plate, the mean constitutive value is subtracted from the mean AEC value for each cytokine-stimulated group (EBM and solvent controls, as well as test substance), resulting in a number which represents upregulated ICAM-1 and inducible VCAM-1 or E-selectin Cell adhesion molecule (CAM) expression (referred to as AEC-CAM). Each AEC-CAM value is then divided by the corresponding mean Giemsa value, resulting in a number which estimates relative levels of CAM expression for a given cell density, based on the number of nuclei (referred to as AEC: Giemsa ratio).

AEC(stimulated)-AEC(unstimulated)=AEC-CAM

AEC-CAM/Giemsa=AEC:Giemsa ratio

Therefore "actual" CAM IC50 values are determined by comparing the AEC:Giemsa values for a test substance with those of the stimulated control (EBM, solvent). These values are then analyzed relative to the IC50 values for Giemsa alone. Strict criteria determine whether the CAM inhibition versus cytotoxicity (Giemsa) profile indicates a "real" hit which should be pursued.

C. HaCaT Cell PROLIFERATION ASSAY

HaCaT cells are cultivated in DMEM (Gibco #074-02100) supplemented with 2.2 g/l $NaHCO_3$, 0.11 g/l sodium pyruvate, 15 mM Hepes, 5% fetal calf serum (FCS), penicillin (100 U/ml), streptomycin (100 µg/ml), and glutamine (to increase the final concentration by 4 mM). For the proliferation assay, cells are detached by trypsinization, suspended in fresh medium, and seeded into 96-well microtiter plates at a final density of 4000 cells/0.2 ml/well. After 24 hours (day 0) the medium is replaced with fresh medium containing graded concentrations of test compound. After 3 days of incubation at 37° C./5% $CO_2$, the extent of cellular proliferation in comparison to solvent controls is measured by a colorimetric assay that measures relative cell mass using the dye sulforhodamine B (Skehan et al, 1990, J. Natl. Cancer Inst. 82, 1107–1112). The "starting cell number" is determined by measuring the relative cell mass on day 0. The results are expressed as % Inhibition=100-% control absorbance (where solvent control=100%) and represent the average±standard deviation of three measurements. A dose-response curve is plotted semi-logarithmically and the concentration required for half-maximal inhibition ($IC_{50}$) is determined by linear interpolation. Maximal inhibition without net loss of cells is represented by the "starting cell number" and is usually between 90–98%.

NMR-Specta ($CDCl_3$)

Example: Spectrum:

4 (3 conformers 55:44:3, major and minor conformer marked with * resp. °): 8.80* (d, J=10 Hz, NH); 7.89* (d, J=10 Hz, NH); 7.78°(d, J=10 Hz, NH); 7.57° (d, J=10 Hz, NH); 7.50*° (d, J=7 Hz, MeMeOTrp H-4'); 7.39*, 7.37° (2d, J=8 Hz, MeMeOTrp H-7'); 7.20*° (m, MeMeOTrp, H-6'); 7.11°, 7.06* (2s, MeMeOTrp H-2'); 7.03*°(2dd, MeMeOTrp H-5'); 6.16° (d, J=10 Hz, Leu NH); 5.95* (d, J=6 Hz, Leu NH); 5.30° (m, al-H); 5.10* (dd, hydoxy-butyric acid al-H); 5.03–4.98 (m, al-H); 4.91 (dd, al-H); 4.85 (m, al-H); 4.71° (m, al-H); 4.45* (dd, al-H); 4.29* (m, al-H); 4.03*, 4.02° (2s, N-OMe); 3.87 (dd); 3.72*, 3.64° (2s, COOMe); 3.63–3.50 (m); 3.47* (q, J=7 Hz, MeAla al-H); 3.41° (s, N-Me); 3.36* (dd, MeMeOTrp β-H); 3.23–3.17 (m); 3.20* (s, MeAla N-Me); 3.19° (s, N-Me); 2.91* (s, MeMeOTrp N-Me); 2.53* (s, MeLeu N-Me); 2.51° (s, MeMeOTrp N-Me); 2.43–2.09 (m); 2.03–1.89 (m); 1.83–1.75 (m); 1.68–1.07 (m); 1.52* (d, J=7 Hz, MeAla β-Me); 1.48° (d,J=7 Hz, MeAla β-Me); 1.04 (d, J=6.5 Hz); 0.98–0.83 (m); 0.53* (d, J=6.6 Hz, Leu Me); 0,01* (d, J=6.6, Leu Me); −0.32 (ddd, J=3.6 Hz, J=11.1 Hz, J=14.5 Hz, Leu β-CH).

4 (open-chain derivative of formula IV): (2 conformers 68:32, major and minor conformer marked with * resp. °): 8.16, 8.12, 8.05, 8.00 (4d, NH); 7.58°,7.55* (2d, J=8 Hz, MeMeOTrp 4'-H); 7.38*° (d, MeMeOTrp H-7'); 7.22*, 7.20° (2m, MeMeOTrp H-6'); 7.15*, 7.12° (2s, MeMeOTrp H-2'); 7.07*, 7.03° (2m, MeMeOTrp H-5'); 6.57 (s br, NH); 5.10° (dd, al-H); 5.17* (dd, hydroxybutyric acid al-H); 5.11*°(m, MeLeu al-H); 5.04*° (dd, al-H); 4.99* (ddd, al-H); 4.88° (ddd, al-H); 4.51° (dd); 4.53* (m, Leu al-H); 4.48° (m); 4.42* (m br, MeAla al-H); 4.05*, 4.03° (2s, N-OMe); 3.88° (q, J=7 Hz, MeAla al-H); 3.71°, 3.68* (2s, COOMe); 3.57*, 3.54° (2s, COOMe); 3.47* (m br,MeMeOTrp al-H); 3.27°, 3.21* (2s, NMe); 3.2 (m, MeMeOTrp β-$H_a$); 3.00* (s, NMe); 2.9 (m, MeMeOTrp β-$H_b$); 2.64° (s, NMe); 2.32*, 2.28° (2s, NMe); 2.33–2.13 (m); 2.20 (m); 1.86 (m); 1.7–1.1 (m); 1.50°, 1.48* (2d, J=7 Hz, MeAla β-Me); 0.97–0.93 (m); 0.90–0.76 (m).

5 (3 conformers 2:2:1, minor conformer marked with *): 8.81 (d, J=10 Hz, NH); 7.93 (d, J=10 Hz, NH); 7.79 (d, J=9 Hz, NH); 7.65 (m br, NH); 7.54 (m, MeMeOTrp H-4'); 7.38, 7.37, 7.34* (3d, J=8 Hz, MeMeOTrp H-7'); 7.19 (m, MeMeOTrp, H-6'); 7.08–6.98 (m, MeMeOTrp H-5'); 7.02 (s, MeMeOTrp H-2'); 6.14 (d, J=10 Hz, Leu NH); 6.29* (d, J=7 Hz, Leu NH); 6.07 (d, J=6 Hz, Leu NH); 5.25 (m, al-H); 5.12–4.92 (al-H); 4.84 (m, al-H); 4.69 (m, al-H); 4.43 (m, al-H); 4.29 (m, al-H); 4.03*, 4.02, 4.00 (3s, N-OMe); 3.98 (m, al-H); 3.63–3.3 (m); 3.39–3.34* (s br NMe); 3.21 (s, NMe); 3.18* (s, NMe); 3.13 (m); 3.07* (s, NMe); 3.04* (s, NMe); 2.91 (s, N-Me); 2.53 (s, NMe); 2.37 (s br, NMe); 2.5–1.05 (m); 1.47, 1.43, 1.41* (3d, J=7 Hz, MeAla β-Me); 1.03 (d, J=6.5 Hz); 0.98–0.83 (m); 0.68*,0.55, 0.47*, −0.02 (4d, J=6.6 Hz, Leu Me); −0.32 (ddd, Leu β-CH).

6 (3 conformers 4:3:1, minor conformer marked with *): 8.82 (d, J=10 Hz, NH); 7.95* (d, J=9.3 Hz, NH); 7.90 (d, J=9.8 Hz, NH); 7.80 (d, J=9.4 Hz, NH); 7.59, 7.53 (2d, J=8 Hz, MeMeOTrp H-4'); 7.45–7.30 (m, MeMeOTrp H-7'); 7.23–7.15 (m, MeMeOTrp H-6'); 7.20, 7.18 (2s, MeMeOTrp H-2'); 7.11–7.03 (m, MeMeOTrp H-5'); 6.86* (q, J=5 Hz, NHMe); 6.23 (d, 9.5 Hz, Leu NH); 5.95 (d, J=6.5 Hz, Leu NH; q, NHMe); 5.84* (d, J=8.9 Hz, Leu NH); 5.55 (q, 5 Hz, NHMe); 5.3–4.95 (m, al-H); 4.84 (ddd, al-H); 4.69 (ddd, al-H); 4.42 (dd, MeLeu al-H); 4.34 (ddd, Leu al-H); 4.05*, 4.03, 4.02 (3s, N-OMe); 3.98 (m, al-H); 3.63–3.52 (m, al-H); 3.47 (q, Ala al-H); 3.37, 3.35*, 3.24*, 3.22, 3.20 (5s, NMe); 3.3–3.2 (m); 3.03*, 2.92 (2s, NMe); 2.85, 2.74, 2.70* (3d, J=5 Hz, NH-Me), 2.53, 2.52 (2s, NMe); 2.23–1.93 (m); 1.85–1.05 (m); 1.53, 1.47, 1.44* (3d, J=7 Hz, MeAla β-Me); 1.03 (d, J=6.5 Hz); 0.98–0.80 (m); 0.57*,0.55, 0.38*, 0.08 (4d, J=6.6 Hz, Leu Me); −0.30 (ddd, Leu β-CH).

7 (3 conformers 40:53:7, marked with * ° '): 8.81* (d, J=10 Hz, $C_9$AA NH); 7.88* (d, J=10 Hz, $C_9$AA NH); 7.78°(d, J=10 Hz, NH); 7.57° (d, J=10 Hz, NH); 7.52*° (2d, J=7 Hz, MeMeOTrp H-4'); 7.39°, 7.37° (2d, J=8 Hz, MeMeOTrp H-7'); 7.27° (s, MeMeOTrp H-2'); 7.20, 7.18 (2m, MeMeOTrp, H-6'); 7.17° (s, MeMeOTrp H-2'); 7.03°, 7.01° (2m, MeMeOTrp H-5'); 6.17° (d, J=10 Hz, Leu NH); 5.98* (d, J=6 Hz, Leu NH); 5.77' (d, J=10 Hz, Leu NH); 5.31° (ddd, MeAla al-H); 5.19* (dd, hydroxybutyric acid al-H); 5.05–4.94 (m, al-H); 4.88–4.83 (m, al-H); 4.70–4.64 (m, al-H); 4.48* (dd, MeLeu al-H); 4.32* (m, Leu al-H); 4.03*, 4.02° (2s, N-OMe); 3.93° (m, al-H); 3.7–3.5 (m, morpholine); 3.5–3.2 (m); 3.40° (s, N-Me); 3.34° (dd, MeMeOTrp H-βa); 3.22 (m, MeMeOTrp H-βb); 3.20°(s, N-Me); 3.17*(s, N-Me); 2.93* (s, MeMeOTrp N-Me); 2.54* (s, MeLeu N-Me); 2.53° (s, N-Me); 2.4–2.35 (m); 2.2–1.9 (m); 1.83–1.05 (m); 1.53*, 1.50° (2d, J=7 Hz, MeAla β-Me); 1.04 (d, J=6.5 Hz, MeLeu Me); 1.00–0.77 (m); 0.57* (d, J=6.6 Hz, Leu Me); 0.52', 0.34' (2d, J=6.6 Hz, Leu Me); 0.09* (d, J=6.6 Hz, Leu Me); –0.25 (ddd, Leu β-CH).

8 (2 conformers 45:55, marked with * °): 8.84' (d, J=10 Hz, C9AA NH); 7.87* (d, J=10 Hz, C9AA NH); 7.77°(d, J=10 Hz, NH); 7.57° (d, J=10 Hz, NH); 7.55*, 7.52° (2d, J=7 Hz, MeMeOTrp H-4'); 7.36*, 7.35° (2d, J=8 Hz, MeMeOTrp H-7'); 7.36*(s, MeMeOTrp H-2'); 7.23* (s, MeMeOTrp H-2'); 7.20, 7.17 (2m, MeMeOTrp H-6'); 7.03°, 7.01* (2m, MeMeOTrp H-5'); 6.17° (d, J=10 Hz, Leu NH); 5.95* (d, J=6 Hz, Leu NH); 5.31° (ddd, MeAla al-H); 5.24* (dd, hydroxybutyric acid al-H); 5.05–4.97 (m, al-H); 4.93 (dd, al-H); 4.87 (dd, al-H); 4.88–4.83 (m, al-H); 4.66–4.60 (m, al-H);4.48* (dd, MeLeu al-H); 4.38* (ddd, Leu al-H); 4.15–4.00 (m); 4.03*, 4.02° (2s, N-OMe); 3.98° (m, al-H); 3.7–3.2 (m); 3.40° (s, N-Me); 3.20° (s, N-Me); 3.17*(s, N-Me); 3.05–2.9 (m); 2.99, 2.98 (2s, CON-Me); 2.96 (s, 2×CON-Me); 2.92* (s, MeMeOTrp N-Me); 2.54 (s, MeLeu N-Me and N-Me); 2.4–2.25 (m); 2.15–1.9 (m); 1.83–1.05 (m); 1.53*, 1.50° (2d, J=7 Hz, MeAla β-Me); 1.04 (d, J=6.5 Hz, MeLeu Me); 1.00–0.83 (m); 0.79°, 0.74° (2d); 0.57* (d, J=6.6 Hz, Leu Me); 0.13* (d, J=6.6 Hz, Leu Me); –0.25 (ddd, Leu β-CH).

9 (3 conformers 70:28:2, marked with * ° '): 8.89* (d, 10 Hz, PrLeu6 NH); 7.89* (d, 10 Hz, PrLeu2 NH); 7.77° (d, 10 Hz, PrLeu6 NH); 7.52° (d, 8 Hz, indole H-4'); 7.50° (d, PrLeu2 NH); 7.48* (d, 8 Hz, indole H-4'); 7.38* (d, 8 Hz, indole H-7'); 7.37° (d, 8 Hz, indole H-7'); 7.19° (dd, indole H-6'); 7.18* (dd, indole H-6'); 7.13° (s, indole H-2'); 7.02* (s, indole H-2'); 6.99° (dd, indole H-5'); 6.90* (dd, indole H-5'); 6.18° (d br, 10 Hz, Leu NH); 5.93* (d, 6 Hz, Leu NH); 5.83' (d, Leu NH); 5.30° (ddd, PrLeu6 α-H); 5.30* (dd, Hba α-H); 5.02* (ddd, PrLeu6 α-H); 5.00° (ddd, PrLeu2 α-H); 4.89* (dd, MeTrp α-H); 4.84* (ddd, PrLeu2 α-H); 4.71° (ddd, α-H); 4.44* (dd, MeLeu α-H); 4.37* (ddd, Leu α-H); 4.03*, 4.02° (2s, N-OMe); 3.63–3.52; 3.49* (q, 7 Hz, MeAla α-H); 3.40° (s, N-Me); 3.38* (dd, MeTrp β-Ha); 3.26–3.20; 3.23* (s, MeAla N-Me); 3.21° (s, N-Me); 2.93* (s, MeTrp N-Me); 2.53* (s, MeLeu N-Me); 2.52° (s, N-Me); 2.45–1.75; 2.33, 2.15 (2m, aziridine)1.56–1.07; 1.50* (d, 7 Hz, MeAla β-Me); 1.47° (d, 7 Hz, MeAla β-Me); 1.03* (d, 6.5 Hz, MeLeu d-Me); 0.98–0.83; 0.48* (d, 6.6 Hz, Leu δ'-Me); –0.13* (d, 6.6 Hz, Leu δ''-Me); –0.48* (ddd, Leu γ-CH).

10 (3 conformers 45:51:4, marked with * ° '): 8.86* (d, 10 Hz, PrLeu6 NH); 7.87* (d, 10 Hz, PrLeu2 NH); 7.75* (d, 10 Hz, PrLeu6 NH); 7.57° (d, 8 Hz, indole H-4'); 7.55° (d, PrLeu2 NH); 7.51° (d, 8 Hz, indole H-4'); 7.41° (s, indole H-2'); 7.38* (d, 8 Hz, indole H-7'); 7.36° (d, 8 Hz, indole H-7'); 7.29* (s, indole H-2'); 7.18* (dd, indole H-6'); 7.17° (dd, indole H-6'); 7.03° (dd, indole H-5'); 7.01* (dd, indole H-5'); 6.17° (d br, 10 Hz, Leu NH); 5.94* (d, 6 Hz, Leu NH); 5.79' (d, Leu NH); 5.30° (ddd, PrLeu6 α-H); 5.27* (dd, α-H); 5.00° (ddd, PrLeu6 α-H); 4.98° (ddd, α-H); 4.93° (dd, α-H); 4.87* (dd, α-H); 4.85* (ddd, PrLeu2 α-H); 4.63° (ddd, α-H); 4.47* (dd, MeLeu α-H); 4.40 (m); 4.02* (ddd, Leu α-H); 4.02, 4.01 (2s, N-OMe); 3.68–3.22; 3.40° (s, N-Me); 3.20° (s, N-Me); 3.18* (s, MeAla N-Me); 2.91* (s, MeTrp N-Me); 2.55° (s, N-Me); 2.53* (s, MeLeu N-Me); 2.35–1.05; 1.54* (d, 7 Hz, MeAla β-Me); 1.50° (d, 7 Hz, MeAla β-Me); 1.03* (d, 6.5 Hz, MeLeu d-Me); 0.98–0.83; 0.78° (d, 6 Hz, Leu δ'-Me); 0.73° (d, 6 Hz, Leu δ''-Me); 0.57* (d, 6.6 Hz, Leu δ'-Me); 0.16* (d, 6.6 Hz, Leu δ''-Me); –0.27* (ddd, Leu γ-CH).

11 (3 conformers 46:51:3 marked with * ° '): 8.87* (d, 10 Hz, PrLeu6 NH); 7.87* (d, 10 Hz, PrLeu2 NH); 7.76° (d, 10 Hz, PrLeu6 NH); 7.56° (d, PrLeu2 NH); 7.55* (d, 8 Hz, indole H-4'); 7.52° (d, 8 Hz, indole H-4'); 7.37 (d, 8 Hz, indole H); 7.36 (d, 8 Hz, indole H); 7.36° (s, indole H-2'); 7.22* (s, indole H-2'); 7.20* (dd, indole H-6'); 7.18* (dd, indole H-6'); 7.03° (dd, indole H-5'); 7.00* (dd, indole H-5'); 6.16° (d, 10 Hz, Leu NH); 5.94* (d, 6 Hz, Leu NH); 5.78' (d, Leu NH); 5.31° (ddd, PrLeu6 α-H); 5.27* (dd, α-H); 5.06–4.80; 4.65 (ddd, α-H); 4.47* (dd, MeLeu α-H); 4.33 (m); 4.03,4.01 (2s, N-OMe); 4.00 (ddd, α-H); 3.75–3.20; 3.40 (s, N-Me); 3.20 (s, N-Me); 3.18* (s, MeAla N-Me); 2.91* (s, MeTrp N-Me); 2.53 (s, N-Me); 2.53° (s, MeLeu N-Me); 2.45–1.07; 1.53* (d, 7 Hz, MeAla β-Me); 1.49° (d, 7 Hz, MeAla β-Me); 1.03* (d, 6.5 Hz, MeLeu d-Me); 0.98–0.83; 0.79 (d, 6 Hz, Me); 0.74 (d, 6 Hz, Me); 0.55* (d, 6.6 Hz, Leu δ'-Me); 0.07* (d, 6.6 Hz, Leu δ''-Me); –0.36* (ddd, Leu β-CH).

12 (4 conformers 27:33:17:33 marked with * ° "): 8.9* (d, 10 Hz, PrLeu6 NH); 8.82' (d, 10 Hz, PrLeu6 NH); 7.9* (d, 10 Hz, PrLeu2 NH); 7.86' (d, 10 Hz, PrLeu2 NH); 7.76° (d, 10 Hz, PrLeu6 NH); 7.75" (d, 10 Hz, PrLeu6 NH); 7.24* (s, indole); 7.03* (dd, indole); 6.17" (d br, 10 Hz, Leu NH); 6.17° (d br, 10 Hz, Leu NH); 6.03' (d, 6 Hz, Leu NH); 5.98* (d, 6 Hz, Leu NH); 4.02" (s); 4.02° (s); 4.02* (s); 4.02' (s); 3.40 (s, N-Me); 3.40 (s, N-Me); 3.20 (s, N-Me); 3.20 (s, N-Me); 3.17 (s, N-Me); 2.97 (s, N-Me); 2.94 (s, N-Me); 2.94 (s, N-Me); 2.93 (s, N-Me); 2.91 (s, N-Me); 2.56 (s, N-Me); 2.56 (s, N-Me); 2.53' (s, MeLeu N-Me); 2.53* (s, MeLeu N-Me); 1.53* (d, 7 Hz, MeAla β-Me); 1.53' (d, 7 Hz, MeAla β-Me); 1.50° (d, 7 Hz, MeAla β-Me); 1.50" (d, 7 Hz, MeAla β-Me); 1.03* (d, 6.5 Hz, MeLeu d-Me); 1.03* (d, 6.5 Hz, MeLeu d-Me); 0.78° (d, 6.6 Hz, Leu δ'-Me); 0.77" (d, 6.6 Hz, Leu δ'-Me); 0.72" (d, 6.6 Hz, Leu δ''-Me); 0.72° (d, 6.6 Hz, Leu δ''-Me); 0.61' (d, 6.6 Hz, Leu δ'-Me); 0.55* (d, 6.6 Hz, Leu δ'-Me); 0.21' (d, 6.6 Hz, Leu δ''-Me); 0.12* (d, 6.6 Hz, Leu δ''-Me); –0.17' (ddd, Leu γ-CH); –0.31* (ddd, Leu γ-CH).

13 (2 conformers 55:45, major and minor conformer marked with * resp. °): 8.80* (d, J=10 Hz, NH); 7.88* (d, J=10 Hz, NH); 7.77°(d, J=10 Hz, NH); 7.57° (d, J=10 Hz, NH); 7.52*, 7.51° (2d, J=7 Hz, MeMeOTrp H-4'); 7.39*, 7.37° (2d, J=8 Hz, MeMeOTrp H-7'); 7.20*° (m, MeMeOTrp, H-6'); 7.16°, 7.09* (2s, MeMeOTrp H-2'); 7.03*°(2dd, MeMeOTrp H-5'); 6.17° (d, J=10 Hz, Leu NH); 5.97* (d, J=6 Hz, Leu NH); 5.31° (m, MeAla al-H); 5.11–4.96 (m, al-H); 4.92* (dd, MeMeOTrp al-H); 4.87 (ddd, al-H); 4.69° (m, Leu al-H); 4.47* (dd, MeLeu al-H); 4.27* (dd, Leu al-H); 4.03*, 4.02° (2s, N-OMe); 3.92 (dd); 3.65–3.15 (m); 3.47* (q, J=7 Hz, MeAla al-H); 3.41° (s, N-Me); 3.21* (s, MeAla NMe); 3.20°(s, N-Me); 2.92* (s, MeMeOTrp N-Me); 2.53° (s, MeLeu N-Me); 2.51° (s, N-Me); 2.35–2.75 (m); 1.7–1.05 (m); 1.53* (d, J=7 Hz, MeAla β-Me); 1.49° (d, J=7 Hz, MeAla β-Me); 1.28*, 1.25*, 1.23*, 1.18° (4d, J=6 Hz, COOCHMe$_2$); 1.04 (d, J=6.5 Hz, MeLeu Me); 0.98–0.83 (m); 0.55* (d, J=6.6 Hz, Leu Me); 0.05* (d, J=6.6 Hz, Leu Me); –0.31 (ddd, Leu β-CH).

14 (3 conformers 55:43:2, marked with * °'): 8.82* (d, J=10 Hz, C₉AA NH); 7.85* (d, J=10 Hz, C₉AA NH); 7.78° (d, J=10 Hz, NH); 7.58° (d, J=10 Hz, NH); 7.52*, 7.51° (2d, J=7 Hz, MeMeOTrp H-4'); 7.39*, 7.37° (2d, J=8 Hz, MeMeOTrp H-7'); 7.22*, 7.21° (2m, MeMeOTrp, H-6'); 7.14°, 7.08* (2s, MeMeOTrp H-2'); 7.03* °(2dd, MeMeOTrp H-5'); 6.17° (d, J=10 Hz, Leu NH); 5.95* (d, J=6 Hz, Leu NH); 5.78' (d, J=10 Hz, Leu NH); 5.31° (ddd, MeAla al-H); 5.12* (dd, hydroxybutyric acid al-H); 5.05–4.98 (m, al-H); 4.91* (dd, MeMeOTrp al-H); 4.86* (ddd, C₉AA al-H) 4.73–4.68 (m, Leu al-H); 4.47* (dd, MeLeu al-H); 4.32–4.26 (m, Leu al-H); 4,25 (dq, J=11 Hz, J=7 Hz, COOCH₂—); 4.15–4.07 (m, COOCH₂—); 4.04*, 4.03° (2s, N-OMe); 3.84° (m, al-H); 3.64–3.50 (m); 3.47* (q, J=7 Hz, MeAla al-H); 3.41° (s, N-Me); 3.34° (dd, MeMeOTrp H-βa); 3.22 (m, MeMeOTrp H-βb); 3.20* (s, MeAla NMe); 3.19°(s, N-Me); 2.93* (s, MeMeOTrp N-Me); 2.53* (s, MeLeu N-Me); 2.52° (s, N-Me); 2.4–2.1 (m); 2.05–1.9 (m); 1.83–1.76 (m); 1.7–1.07 (m); 1.53*, 1.49° (2d, J=7 Hz, MeAla β-Me) ;1.30, 1.25 (2t, J=7 Hz, COOCH2CH3); 1.04 (d, J=6.5 Hz, MeLeu Me); 1.00–0.84 (m); 0.55* (d, J=6.6 Hz, Leu Me); 0.03* (d, J=6.6 Hz, Leu Me); −0.32 (ddd, Leu β-CH).

15 (3 conformers 57:41:2, marked with * °'): 8.82* (d, J=10 Hz, C₉AA NH); 7.90* (d, J=10 Hz, C₉AA NH); 7.78° (d, J=10 Hz, NH); 7.58° (d, J=10 Hz, NH); 7.52*° (2d, J=7 Hz, MeMeOTrp H-4'); 7.39*, 7.38° (2d, J=8 Hz, MeMeOTrp H-7'); 7.22*, 7.21° (2m, MeMeOTrp, H-6'); 7.14°, 7.08* (2s, MeMeOTrp H-2'); 7.03°, 7.02* (2m, MeMeOTrp H-5'); 6.17° (d, J=10 Hz, Leu NH); 5.98* (d, J-6 Hz, Leu NH); 5.82' (d, J=10 Hz, Leu NH); 5.31° (ddd, MeAla al-H); 5.12* (dd, hydroxybutyric acid al-H); 5.05–4.98 (m, al-H); 4.91* (dd, MeMeOTrp al-H); 4.86* (ddd, C₉AA al-H) 4.73–4.68 (m, Leu al-H); 4.47* (dd, MeLeu al-H); 4.28* (m, Leu al-H); 4.2–3.95 (m, COOCH₂); 4.03*, 4.02° (2s, N-OMe); 3.90° (m, al-H); 3.64–3.42 (m); 3.47* (q, J=7 Hz, MeAla al-H); 3.41° (s, N-Me); 3.34° (dd, MeMeOTrp H-βa); 3.22 (m, MeMeOTrp H-βb); 3.20* (s, MeAla NMe); 3.19°(s, N-Me); 2.93* (s, MeMeOTrp N-Me); 2.53* (s, MeLeu N-Me); 2.52° (s, N-Me); 2.4–2.1 (m); 2.03–1.9 (m); 1.83–1.76 (m); 1.72–1.58 (m, COOCH₂CH₂CH₃); 1.55–1.07 (m); 1.53*, 1.49° (2d, J=7 Hz, MeAla β-Me); 1.04 (d, J=6.5 Hz, MeLeu Me); 1.00–0.84 (m); 0.54* (d, J=6.6 Hz, Leu Me); 0.02* (d, J=6.6 Hz, Leu Me); −0.34 (ddd, Leu β-CH).

16 (2 conformers 70:30, marked with * resp. °): 8.92*, 7.87* 7.75°, 7.58° (4d, J=10 Hz, NH); 7.49* (d, J=8 Hz, MeMeOTrp H-4'); 7.37* (d, J=8 Hz, MeMeOTrp H-7'); 7.20* (dt, MeMeOTrp H-6'); 7.18°, 7.03* (2s, MeMeOTrp H-2'); 7.03°, 6.97* (2 dt, MeMeOTrp H-5'); 6.20* (d, J=10 Hz, Leu NH); 5.96* (d, J=7 Hz, Leu NH); 5.33* (m, hydroxybutyric acid al-H); 5.02 (m, al-H); 4.90* (dd, al-H); 4.83* (ddd, al-H): 4.79* (dd, al-H); 4.70° (m, al-H); 4.39* (dd, al-H); 4.38* (m, al-H); 4.03* (s, N-OMe); 3.92° (m); 3.63–3.53 (m); 3.44–3.40 (m); 3.39°, 3.20° (2s, NMe); 3.32–3.18 (m); 3.17* (s, MeAla NMe); 2.94* (s, MeMeOTrp NMe); 2.53* (s, MeLeu NMe); 2.52* (s, NMe); 2.5–2.3 (m); 2.1–1.1 (m); 2.17*, 2.11° (2s, COMe); 1.51*, 1.48° (2d, J=7 Hz, MeAla β-Me); 1.03* (d, J=6.5 Hz); 0.98–0.83 (m); 0.52* , −0.11* (d, J=6.6 Hz, Leu Me); −0.39* (ddd, Leu β-CH).

17 (3 conformers 45:40:15, marked with * ° '): 8.78° (d, J=9.9 Hz, NH); 7.83* (d, J=9,7 Hz, NH); 7.76' (d, NH); 7.59' (d, J=7.8 Hz, MeMeOTrp H-4'); 7.57 (d, J=9.5 Hz, NH); 7.56, 7.53 (2d, J=8 Hz, MeMeOTrp H-4'); 7.46' (s, MeMeOTrp H-2'); 7.42*, 7.39°, 7.34' (3d, J=8.2 Hz, MeMeOTrp H-7); 7.24*, 7.22°, 7.18' (3t, MeMeOTrp H-6'); 7.11*, 7.08', 7.06° (3t, MeMeOTrp H-5'); 7.04*, 7.03° (2s, MeMeOTrp H-2'); 6.25° (d, J=9.5 Hz, Leu NH); 6.03* (d, J=7 Hz, Leu NH); 5.99' (d, J=8.8 Hz, Leu NH); 5.28* (m, al-H); 5.13' (t, J=4 Hz, OH); 5.09–4.98 (m, al-H); 5.02 (t, J=4 Hz, OH); 4.97 (dd, al-H), 4.88 (dd, al-H); 4.84 (m, al-H); 4.78–4.70 (m, al-H); 4.41 (dd, MeLeu al-H); 4.18 (ddd, Leu al-H); 4.04, 4.02 (2s, N-OMe); 3.78 (m, al-H); 3.65–3.35 (m); 3.42°, 3.32', 3.22*, 3.20° (4s, NMe); 3.17–3.08 (m); 3.03', 2.92', 2.90*, 2.52*, 2.51° (5s, NMe); 2.01–1.1 (m); 1.53, 1.49, 1.40' (3d, J=7 Hz, MeAla β-Me); 1.04 (d, J=6.5 Hz); 0.98–0.83 (m); 0.72', 0.60*, 0.56', 0.03° (4d, J=6.6 Hz, Leu Me); −0.16 (ddd, Leu β-CH).

18 (3 conformers 73:20:7, marked with * ° '): 8.54° (d, J=10 Hz, NH); 8.38' (s br, MeTrp N'-H); 8.26*, 8.17° (2d br, J=2 Hz, MeTrp N'-H); 8.13*, 8.03°, 8.01' (3d, J=9.7 Hz, NH); 7.78* (d, J=7.7 Hz, MeTrp H-4'); 7.74', 7.70', 7.63°, 7.63° (4d); 7.46*, 7.44°, 7.40' (3d, J=8 Hz MeTrp H-7'); 7.27* (dt, MeTrp H-6'); 7.20*, 7.17° (2dt, MeTrp H-5'); 7.09°, 7.03* (2d, J=2 Hz, MeTrp H-2); 6.33° (d, J=10 Hz, Leu NH); 6.17° (d, J=7.4 Hz, Leu NH); 5.97' (d, J=9 Hz, Leu NH); 5.38° (m, al-H); 5.27* (dd, hydroxybutyric acid al-H); 5.21° (dd, al-H); 5.12* (ddd, al-H); 5.07* (dd, al-H); 4.96* (ddd, al-H); 4.87 (m); 4.55* (dd, MeLeu al-H); 4.29* (ddd, Leu al-H); 3.85–3.25 (m); 3.76* (q, J=7 Hz, MeAla al-H); 3.49°, 3.36' (2s, NMe); 3.13* (s, MeAla NMe); 3.29°, 3.13' (2s NMe); 3.02* (s, MeTrp NMe); 2.62° (s, NMe); 2.60* (s, MeLeu NMe); 2.38–1.15 (m); 1.62*, 1.56°, 1.51' (3d, J=7 Hz, MeAla β-Me); 1.13* (d, J=6.5 Hz MeLeu); 1.07–0.93 (m); 0.73', 0.63*, 0.58', 0.02* (4d, J=6.6 Hz, Leu Me); −0.28* (ddd, Leu β-CH).

19 (3 conformers 67:29:4, marked with * ° '): 9.52* (t, J=1.5 Hz, CHO); 9.41° (t, J=1 Hz, CHO); 9.05' (m, CHO); 8.73* (d, J=10 Hz, C₉AA NH); 7.86* (d, J=10 Hz, C₉AA NH); 7.77* (d, J=10 Hz, NH); 7.60* (d, J=10 Hz, NH); 7.47*° (2d, J=7 Hz, MeMeOTrp H-4'); 7.38*° (2d, J=8 Hz, MeMeOTrp H-7'); 7.20*° (2t, MeMeOTrp, H-6'); 7.15°, 7.04* (2s, MeMeOTrp H-2'); 7.03°(m, MeMeOTrp H-5'); 7.00* (dd, MeMeOTrp H-5); 6.22° (d, J=10 Hz, Leu NH); 6.02* (d, J=6 Hz, Leu NH); 5.87' (d, J=10 Hz, Leu NH); 5.29° (ddd, MeAla al-H); 5.17* (dd, hydroxybutyric acid al-H); 5.03–4.93 (m, al-H); 4.91* (dd, MeMeOTrp al-H); 4.84* (ddd, C₉AA al-H); 4.79–4.64° (m, Leu al-H); 4.43* (dd, MeLeu al-H); 4.35* (ddd, Leu al-H); 4.04', 4.03*, 4.02° (3s, N-OMe); 3.81° (m, al-H); 3.63° (dd); 3.57–3.50 (m); 3.48–3.42 (m); 3.43* (q, J=7 Hz, MeAla al-H); 3.38° (s, N-Me); 3.30–3.12 (m); 3.20° (s,N-Me); 3.15* (s, MeAla NMe); 2.93* (s, MeMeOTrp N-Me); 2.58° (s, N-Me); 2.53* (s, MeLeu N-Me); 2.25 (m, CH₂—CHO); 2.15–1.9 (m); 1.85–1.74 (m); 1.65–1.08 (m); 1.48*, 1.45° (2d, J=7 Hz, MeAla β-Me); 1.04* (d, J=6.5 Hz, MeLeu Me); 0.98–0.83 (m); 0.67', 0.58*, 0.52', 0.01* (4d, J=6.6 Hz, Leu Me); −0.20* (ddd, Leu β-CH).

20 (2 conformers 1:1): 8.77 (d, J=10 Hz, C₉AA NH); 7.79 (d, J=10 Hz, C₉AA NH); 7.73 (d, J=10 Hz, NH); 7.65 (d, J=10 Hz, NH); 7.44, 7.44, 7.42, 7.39 (4d, MeMeOTrp H-4' and H-7'); 7.25, 7.22 (2t, MeMeOTrp, H-6'); 7.13–7.03 (m, MeMeOTrp H-5'); 7.02, 6.98 (2s, MeMeOTrp H-2'); 6.19 (d, J=10 Hz, Leu NH); 6.00 (d, J=6 Hz, Leu NH); 5.80–5.53 (m, olefin-H); 5.31 (ddd, MeAla al-H); 5.08–4.67 (m, al-H, olefin-H); 4.47 (dd, MeLeu al-H); 4.15–3.98 (m); 4.05, 4.02 (2s, N-OMe); 3.7–3.0 (m); 3.44, 3.21, 3.20, 2.92, 2.52, 2.44 (6s, N-Me); 2.15–1.90 (m); 1.90–1.08 (m); 1.55, 1.50 (2d, J=7 Hz, MeAla β-Me); 1.05 (d, J=6.5 Hz, MeLeu Me); 1.0–0.8 (m); 0.60, 0.06 (2d, J=6.6 Hz, Leu Me); −0.20 (ddd, Leu β-CH).

21 (3 conformers 44:53:3 marked with * ° '): 8.81* (d, 10 Hz, PrLeu6 NH); 7.78, 7.73, 7.67 (3d, 10 Hz, NH); 7.43, 7.42 (2d, 8 Hz, indole H-4'); 7.37 (d, 8 Hz, indole H-7'); 7.28–7.00; 7.02, 6.97 (2s, indole H-2'); 6.21° (d, 10 Hz, Leu NH); 5.97* (d, 6 Hz, Leu NH); 5.75' (d, Leu NH); 5.50–4.65; 4.47* (dd, MeLeu α-H); 4.05 (ddd, α-H); 4.04 (s, OMe); 4.02 (s, OMe); 3.65–3.10; 3.44° (s, MeAla N-Me); 3.22 (s, MeAla N-Me); 3.19 (s, N-Me); 2.93* (s, MeTrp N-Me); 2.52, 2.39 (2s, N-Me); 2.15–0.82; 1.54*, 1.50° (2d, 7 Hz, MeAla β-Me); 1.04* (d, 6.5 Hz, MeLeu d-Me); 0.57* (d, 6.6 Hz, Leu δ'-Me); 0.48' (d, Leu δ'-Me); 0.26' (d, Leu δ"-Me); −0.04* (d, 6.6 Hz, Leu δ"-Me).

22 (3 conformers 47:48:5, marked with * ° '): 8.63, 7.87, 7.77, 7.63 (4d, 10 Hz, PrLeu NH); 7.49* (d, 7 Hz, indole H-4'); 7.48° (d, 7 Hz, indole H-4'); 7.43* (d, 8 Hz, indole H-7'); 7.41° (d, 8 Hz, indole H-7'); 7.27* (dd, indole H-6'); 7.23° (dd, indole H-6'); 7.13* (dd, indole H-5'); 7.08° (dd, indole H-5'); 7.04° (s, indole H-2'); 7.02* (s, indole H-2'); 6.98' (s, indole H-2'); 6.20° (d, 10 Hz, Leu NH); 6.01* (d, 7 Hz, Leu NH); 5.79' (d, 9 Hz, Leu NH); 5.30° (ddd, PrLeu6 α-H); 5.07* (dd, Hba α-H); 5.03* (ddd, PrLeu6 α-H); 4.86* (ddd, PrLeu2 α-H); 4.79 (dd, MeTrp α-H); 4.47* (dd, MeLeu α-H); 4.18* (ddd, Leu α-H); 4.06 (s, N-OMe); 4.05' (s, N-OMe,); 4.03 (s, N-OMe); 3.71–3.50; 3.42 (s, N-Me); 3.23–3.05; 3.20 (s, N-Me); 3.18 (s, N-Me); 2.92 (s, N-Me); 2.52 (s, N-Me); 2.51 (s, N-Me); 2.03–1.08; 1.54* (d, 7 Hz, MeAla β-Me); 1.50° (d, 7 Hz, MeAla β-Me); 1.05* (d, 6.5 Hz, MeLeu d-Me); 0.98–0.84; 0.63* (d, 6.6 Hz, Leu δ'-Me); 0.53' (d, 7 Hz, Leu δ'-Me); 0.34' (d, 7 Hz, Leu δ"-Me); 0.11* (d, 6.6 Hz, Leu δ"-Me); −0.13* (ddd, Leu γ-CH).

23 (3 conformers 40:40:20, marked with * ° '): 8.50* (d, 10 Hz, PrLeu6 NH); 8.20 (m); 7.98* (d, 10 Hz, PrLeu2 NH); 7.57* (d, 8 Hz, indole H-4'); 7.53–7.35; 7.25–7.18; 7.23* (s, indole H-2'); 7.13–7.06; 7.05° (s, indole H-2'); 6.69 (d); 6.29 (d, br); 6.22 (d, br); 6.14° (d, 7 Hz, Leu NH); 6.07* (d, 9 Hz, Leu NH); 5.5° (ddd, PrLeu6 α-H); 5.26–4.63 (m, α-H); 4.36 (m, MeLeu α-H); 4.18* (ddd, Leu α-H); 4.04 (s, OMe); 4.03' (s, OMe,); 4.02 (s, OMe); 3.68–2.78; 3.34 (s, N-Me); 3.19 (s, N-Me); 3.12 (s, N-Me); 3.03 (s, N-Me); 2.91 (s, N-Me); 2.53 (s, N-Me); 2.10–1.05; 1.03–0.78; 0.76 (d); 0.71 (d, 6.5 Hz, Leu g-Me); 0.60 (d, 6.6 Hz, Leu g-Me); 0.08 (d, 6.6 Hz, Leu g-Me); −0.10 (ddd, Leu γ-CH).

24 (3 conformers 43:47:5, marked with * ° ') 8.68* (d, 10 Hz, PrLeu6 NH); 7.87* (d, 10 Hz, PrLeu2 NH); 7.80° (d, 10 Hz, NH); 7.63° (d, 10 Hz, NH); 7.55–7.37 (m, indole); 7.27–7.10 (m, indole); 7.08° (s, indole H-2'); 7.03* (s, indole H-2'); 6.58 (t, 8 Hz C=C,); 6.23 (t, 8 Hz C=C,); 6.18° (d, 6.7 Hz, Leu NH); 6.03* (d, 10 Hz, Leu NH); 5.80' (d, Leu NH); 5.31° (ddd, PrLeu6 α-H); 5.08–4.91 (α-H); 4.86* (ddd, PrLeu2 α-H); 4.77–4.68 M, α-H); 4.46* (dd, MeLeu α-H); 4.14* (ddd, Leu α-H); 4.05° (s, OMe); 4.03* (s, OMe); 4.02' (s, OMe,); 3.71° (q, 7 Hz, MeAla α-H); 3.60* (q, 7 Hz, MeAla α-H); 3.53–3.00; 3.44° (s, MeAla N-Me); 3.23 (s, N-Me); 3.20 (s, N-Me); 2.93* (s, MeTrp N-Me); 2.52 (s, N-Me); 2.44 (s, N-Me); 2.20–0.83; 1.56* (d, 7 Hz, MeAla β-Me); 1.51° (d, 7 Hz, MeAla β-Me); 1.05* (d, 6.5 Hz, MeLeu d-Me); 0.62* (d, 6.6 Hz, Leu δ'-Me); 0.57' (d, Leu δ'-Me); 0.40' (d, Leu δ"-Me); 0.10* (d, 6.6 Hz, Leu δ"-Me); −0.17* (ddd, Leu γ-CH).

25 (3 conformers 51:45:4, marked with * ° '): 8.68* (d, 10 Hz, PrLeu6 NH); 7.87* (d, 10 Hz, PrLeu2 NH); 7.81* (d, 10 Hz, PrLeu6 NH); 7.63° (d, 10 Hz, PrLeu2 NH); 7.53 (d, 8 Hz, indole H-4'); 7.51 (d, 8 Hz, indole H-4'); 7.43 (d, 8 Hz, indole H-7'); 7.40 (d, 8 Hz, indole H-7'); 7.26 (dd, indole H-6'); 7.23 (dd, indole H-6'); 7.13 (dd, indole H-5'); 7.07° (s, indole H-2'); 7.07 (dd, indole H-5'); 7.03* (s, indole H-2'); 6.21° (d, 10 Hz, Leu NH); 6.05* (d, 6 Hz, Leu NH); 5.79' (d, 10 Hz, Leu NH); 5.32° (ddd, PrLeu6 α-H); 5.14* (dd, Hba α-H); 5.03* (ddd, PrLeu6 α-H); 4.87* (ddd, PrLeu2 α-H); 4.83* (dd, MeTrp α-H); 4.77° (ddd, Leu α-H); 4.51* (dd, MeLeu α-H); 4.13* (ddd, Leu α-H); 4.06° (s, OMe); 4.03* (s, OMe); 3.68 (m); 3.57* (q, 7 Hz, MeAla α-H); 3.44° (s, MeAla N-Me); 3.36* (dd, MeTrp β-Ha); 3.23 (dd, MeTrp β-Hb); 3.22 (s, N-Me); 3.17 (s, N-Me); 3.14 (dd); 2.96 (m CCH,); 2.93* (s, MeTrp N-Me); 2.53 (s, N-Me); 2.49 (s, N-Me); 2.25–1.97; 1.86–1.78; 1.55* (d, 7 Hz, MeAla β-Me); 1.52* (d, 7 Hz, MeAla β-Me); 1.50–1.09; 1.06* (d, 6.5 Hz, MeLeu d-Me); 1.00–0.85; 0.63* (d, 6.6 Hz, Leu δ'-Me); 0.58* (d, Leu δ'-Me); 0.38' (d, Leu δ"-Me); 0.07* (d, 6.6 Hz, Leu δ"-Me); −0.11* (ddd, Leu γ-CH).

26 (6:4 mixture of E/Z isomers with 3 conformers each, only characteristic signals given): 8.61, 8.48, 7.93, 7.84, 7.82, 7.74, (d, 10 Hz, PrLeuNH); 7.52 (d, 8 Hz, indole); 7.08 s ( indole H-2'); 6.44, 6.22 (2dt, CH=CHCN); 6.36–6.26 (m); 6.13, 6.07, 5.87 (3d, Leu NH); 5.33–5.28 (m); 5.24, 5.20 (2dm, CH=CHCN); 5.06–4.97 (m); 4.92 (2d); 4.87–4.75 (m);4.49, 4.46 (2dd, MeLeu α-H); 4.28, 4.18 (2ddd, Leu α-H); 4.07, 4.06, 4.05, 4.03 (4s, N-OMe); 3.88, 3.82 (2q, 7 Hz, MeAla α-H); 3.43, 3.40, 3.23, 3.21, 3.19, 3.12, 2.93, 2.55, 2.53, 2.52, 2.51 (11s, N-Me); 1.54–1.49 (5d, MeAla β-Me); 1.06, 1.04 (2d, 7 Hz, MeLeu d-Me); 0.74, 0.65, 0.52, 0.26, 0.08 (5d, Leu g-Me); −0.04 (ddd, Leu γ-CH).

27 (3 conformers 51:46:3 marked with * ° '): 8.71* (d, 10 Hz, PrLeu6 NH); 7.90* (d, 10 Hz, PrLeu2 NH); 7.76° (d, 10 Hz, PrLeu6 NH); 7.60 (d, 10 Hz, PrLeu2 NH); 7.52* (d, 8 Hz, indole H-4'); 7.48° (d, 8 Hz, indole H-4'); 7.42 (d, 8 Hz, indole); 7.40 (d, 8 Hz, indole); 7.26* (dd, indole H-6'); 7.13* (dd, indole H-5'); 7.07° (dd, indole H-5'); 7.03* (s, indole H-2); 7.02° (s, indole H-2); 6.16° (d br, 10 Hz, Leu NH); 6.01* (d, 6 Hz, Leu NH); 5.77' (d, Leu NH); 5.31 (ddd, α-H); 5.05–4.97; 4.86 (ddd, α-H); 4.82 (dd, α-H); 4.74 (m); 4.46* (dd, MeLeu α-H); 4.17* (ddd, Leu α-H); 4.05* (s, N-OMe); 4.03° (s, N-OMe); 3.68 (m); 3.57 (m); 3.47 (m, CH2Cl,); 3.43 (s, N-Me); 3.28* (dd, MeTrp β-Ha); 3.23* (s, MeAla N-Me); 3.21 (s, N-Me); 3.20* (dd, MeTrp β-Hb); 2.92* (s, MeTrp N-Me); 2.53* (s, MeLeu N-Me); 2.49 (s, N-Me); 2.23° (dd, indole H-6'); 2.05–1.1; 1.54* (d, 7 Hz, MeAla β-Me); 1.50° (d, 7 Hz, MeAla β-Me); 1.05* (d, 6.5 Hz, MeLeu d-Me); 0.98–0.85; 0.57* (d, 6.6 Hz, Leu δ'-Me); 0.52' (d, Leu δ'-Me); 0.28' (d, Leu δ"-Me); 0.06* (d, 6.6 Hz, Leu δ"-Me); −0.32* (ddd, Leu γ-CH).

28 (3 conformers 37:59:4 marked with * ° '): 8.73* (d, 10 Hz, PrLeu6 NH); 7.8* (d, 10 Hz, PrLeu2 NH); 7.73° (d, 10 Hz, PrLeu6 NH); 7.63° (d, 10 Hz, PrLeu2 NH); 7.49° (d, 8 Hz, indole H-4'); 7.47* (d, 8 Hz, indole H-4'); 7.42* (d, 8 Hz, indole H-7'); 7.38° (d, 8 Hz, indole H-7'); 7.25 (dd, indole); 7.22° (dd, indole H-6'); 7.12* (dd, indole H-5'); 7.06° (dd, indole H-5'); 7.04 (s, indole H-2'); 7.03 (s, indole H-2'); 6.22° (d br, 10 Hz, Leu NH); 6.00* (d, 6 Hz, Leu NH); 5.78' (d, Leu NH); 5.31° (ddd, PrLeu6 α-H); 5.07 (dd, α-H); 5.05–4.90; 4.87 (ddd, α-H); 4.79 (dd, α-H); 4.72 (m); 4.49* (dd, MeLeu α-H); 4.11* (ddd, Leu α-H); 4.05* (s, N-OMe); 4.03° (s, N-OMe); 3.75–3.50; 3.43 (s, N-Me); 3.38–3.13; 3.28 (s, OMe); 3.28 (s, OMe); 3.23 (s, N-Me); 3.21° (s, N-Me); 2.92* (s, MeTrp N-Me); 2.53* (s, MeLeu N-Me); 2.48° (s, N-Me); 2.00–1.08; 1.55* (d, 7 Hz, MeAla β-Me); 1.50° (d, 7 Hz, MeAla β-Me); 1.05* (d, 6.5 Hz, MeLeu d-Me);

0.98–0.85; 0.60* (d, 6.6 Hz, Leu δ'-Me); 0.05* (d, 6.6 Hz, Leu δ"-Me); −0.18* (ddd, Leu γ-CH).

29 (2 conformers 50:50 marked with * °): 8.70* (d, 10 Hz, PrLeu6 NH); 7.80* (d, 10 Hz, PrLeu2 NH); 7.71° (d, 10 Hz, PrLeu6 NH); 7.69° (d, 10 Hz, PrLeu2 NH); 7.47–7.35; 7.24 (dd, indole); 7.21 (dd, indole); 7.04 (dd, indole); 7.01 (dd, indole); 7.01 (s, indole H-2'); 6.97 (s, indole H-2'); 6.25° (d br, 10 Hz, Leu NH); 6.00* (d, 6 Hz, Leu NH); 5.30° (ddd, PrLeu6 α-H); 5.10–4.69; 4.49* (dd, MeLeu α-H); 4.07* (ddd, Leu α-H); 4.04* (s); 4.02° (s); 3.72–3.02; 3.41 (s, N-Me); 3.20 (s, N-Me); 3.20* (s, MeAla N-Me); 2.91* (s, MeTrp N-Me); 2.53 (s, N-Me); 2.45 (s, N-Me); 2.07–0.82; 1.55* (d, 7 Hz, MeAla β-Me); 1.50° (d, 7 Hz, MeAla β-Me); 1.04* (d, 6.5 Hz, MeLeu d-Me); 0.6* (d, 6.6 Hz, Leu δ'-Me); 0.41 (m, cyPr); −0.03* (d, 6.6 Hz, Leu δ"-Me); −0.24* (ddd, Leu γ-CH).

30 (3 conformers 63:35:2 marked with * ° '): 8.78° (d, 10 Hz, PrLeu6 NH); 7.93*, 7.77° (2d, 10 Hz, PrLeu2 NH); 7.47* (d, 8 Hz, indole H-7'); 7.43* (d, 8 Hz, indole H-4'); 7.40–7.23; 7.17°, 7.13* (2dd, indole H-6'); 7.04, 7.03 (2s, indole H-2'); 6.93° (dd, indole H-5'); 6.97, 6.93 (2s, CH-Ph2,); 6.74* (dd, indole H-5'); 6.14° (d, 10 Hz, Leu NH); 5.92* (d, 6 Hz, Leu NH); 5.78' (d, Leu NH); 5.27° (ddd, PrLeu6 α-H); 5.12* (dd, Hba α-H); 4.98* (ddd, PrLeu6 α-H); 4.96* (dd, MeTrp α-H); 4.85* (ddd, PrLeu2 α-H); 4.70° (ddd, α-H); 4.47* (dd, MeLeu α-H); 4.18* (ddd, Leu α-H); 4.00*, 3.97* (2s, OMe); 3.57° (dd, MeTrp β-Ha); 3.53° (dd, MeTrp β-Hb); 3.37* (dd, MeTrp β-Ha); 3.27* (dd, MeTrp β-Hb); 3.20, 3.19, 2.93, 2.83 (4s, N-Me); 2.66 (q, 7 Hz); 2.55–2.33; 2.52 (s, N-Me); 2.46 (s, N-Me); 2.27–1.92; 1.80 (m); 1.68–1.05; 1.35*, 1.28* (2d, 7 Hz, MeAla β-Me); 1.03* (d, 6.5 Hz, MeLeu d-Me); 0.96–0.83; 0.53' (d, Leu δ'-Me); 0.49* (d, 6.6 Hz, Leu δ'-Me); 0.32' (d, Leu δ"-Me); −0.12* (d, 6.6 Hz, Leu δ"-Me); −0.49* (ddd, Leu γ-CH).

31 (mixture of conformers, only selected signals given): 7.13, 7.03 (2s, indole H-2'); 4.56, 4.40 (2m, α-H); 4.03 (s, N-OMe); 3.42, 3.23, 3.07, 2.94, 2.53 (5s, N-Me); 0.57, 0.53, (2d, 6.6 Hz, Leu δ'-Me); 0.17, 0.03 (2d, 6.6 Hz, Leu δ"-Me); −0.03, −0.27 (2ddd, Leu β-CH).

32 (3 conformers 78:16:6, marked with * ° '): 8.45* (d, J=10 Hz, PrLeu6 NH); 8.04* (d, J=10 Hz, PrLeu2NH); 7.83° (d, J=10 Hz, NH); 7.68*, 7.53° (2d, J=7 Hz, indole H-4'); 7.30* (d, J=8 Hz, indole H-7'); 7.23* (m, indole H-6'); 7.10* (dd, indole H-5'); 6.87°, 6.79* (2s, indole H-2'); 6.28° (d, J=10 Hz, Leu NH); 6.07* (d, J=6 Hz, Leu NH); 5.83' (d, J=10 Hz, Leu NH); 5.31° (ddd, PrLeu α-H); 5.18* (dd, Hba α-H); 5.13° (dd, Hba α-H); 5.05* (ddd, PrLeu6 α-H); 4.98° (ddd, Leu α-H); 4.93* (dd, MeTrp α-H); 4.84* (ddd, PrLeu2 α-H); 4.78° (ddd, PrLeu2 α-H); 4.47* (dd, MeLeu α-H); 4.13* (ddd Leu α-H); 3.8–3.5 (m); 3.72*° (2s, MeTrp N1'-Me); 3.69* (q, J=7 Hz, MeAla α-H); 3.40° (s, MeAla N-Me); 3.28* (s, MeAla N-Me); 3.2° (dd, MeTrp β-Hb); 3.12* (dd, MeTrp β-Ha); 2.93* (s, MeTrp, N-Me); 2.53° (s, N-Me); 2.52* (s, MeLeu N-Me); 3.21° (s, N-Me); 2.25–2.08 (m, Hba γ-CH₂, β-Ha); 1.92* (m, Hba β-Hb); 1.83–1.75 (m); 1.7–1.07 (m); 1.53*, 1.48° (2d, J=7 Hz, MeAla β-Me); 1.04 (d, J=6.5 Hz, MeLeu δ-Me); 0.97–0.84 (m); 0.53* (d, J=6.6 Hz, Leu Me); 0.28' (d); −0.17* (d, J=6.6 Hz, Leu Me); −0.53* (ddd, Leu γ-CH).

33 (3 conformers 80:14:6, marked with * ° '): 8.48* (d, 10 Hz, PrLeu6 NH); 8.06* (d, 10 Hz, PrLeu2 NH); 7.94° (d, 10 Hz, PrLeu NH); 7.68* (d, 8 Hz, indole H-4'); 7.54° (d, indole); 7.33* (d, 8 Hz, indole H-7'); 7.31° (d, 8 Hz, indole); 7.22* (dd, indole H-6'); 7.1* (dd, indole H-5'); 7.53° (d, PrLeu NH); 6.93° (s, indole H-2'); 6.84* (s, indole H-2'); 6.26* (d, br, Leu NH); 6.05* (d, 7.5 Hz, Leu NH); 5.84' (d, Leu NH); 5.31° (ddd, PrLeu6 α-H); 5.18* (dd, Hba α-H); 5.13* (dd, Hba α-H); 5.06' (ddd, PrLeu6 α-H); 4.99° (ddd, Leu α-H); 4.93 (dd, MeTrp α-H); 4.87* (ddd, PrLeu2 α-H); 4.8° (ddd, PrLeu2 α-H); 4.47* (dd, MeLeu α-H); 4.16* (ddd, Leu α-H); 4.1* (m, N-CH2); 3.78–3.57; 3.69* (q, 7 Hz, MeAla α-H); 3.47–2.90; 3.42° (s, MeAla N-Me); 3.32* (dd, MeTrp β-Ha); 3.3* (s, MeAla N-Me); 3.23* (dd, MeTrp β-Hb); 3.21° (s, N-Me); 3.06' (s, N-Me); 2.93* (s, MeTrp N-Me); 2.53* (s, MeLeu N-Me); 2.52° (s, N-Me); 2.32–2.10; 1.93* (m, Hba γ-CHb); 1.83–1.08; 1.53* (d, 7 Hz, MeAla β-Me); 1.48° (d, 7 Hz, MeAla β-Me); 1.04* (d, 6.5 Hz, MeLeu d-Me); 0.97–0.84; 0.52* (d, 6.6 Hz, Leu δ'-Me); 0.26' (d, Leu δ"-Me); −0.17* (d, 6.6 Hz, Leu δ"-Me); −0.55* (ddd, Leu γ-CH).

34 (3 conformers 71:24:5, marked with * ° ') 8.50* (d, 10 Hz, PrLeu6 NH); 8.06* (d, 10 Hz, PrLeu2 NH); 7.94° (d, 10 Hz, PrLeu NH); 7.77° (d, 8 Hz, indole H-4'); 7.72* (d, 8 Hz, indole H-4'); 7.53° (d, 10 Hz, PrLeu NH); 7.40–7.05, 6.92° (s, indole H-2'); 6.88* (s, indole H-2'); 6.23° (d, 9.4 Hz, Leu NH); 6.09* (d, 7.4 Hz, Leu NH); 5.87' (d, Leu NH); 5.32° (ddd, PrLeu6 α-H); 5.23* (AB; N1'-CH2); 5.20* (AB; N1'-CH2); 5.17* (dd, Hba α-H); 5.14° (dd, Hba α-H); 5.04* (ddd, PrLeu6 α-H); 4.99° (ddd, PrLeu2 α-H); 4.96* (dd, MeTrp α-H); 4.87* (ddd, PrLeu2 α-H); 4.78° (ddd, Leu α-H); 4.47* (dd, MeLeu α-H); 4.21* (ddd, Leu α-H); 3.76° (q, 7 Hz, MeAla α-H); 3.73–3.65, 3.67* (q, 7 Hz, MeAla α-H); 3.58° (dd, MeLeu α-H); 3.50–3.37, 3.42° (s, MeAla N-Me); 3.33* (dd, MeTrp β-Ha); 3.27* (s, MeAla N-Me); 3.23° (s, N-Me); 3.23* (dd, MeTrp β-Hb); 2.92* (s, MeTrp N-Me); 2.53* (s, MeLeu N-Me); 2.52° (s, N-Me); 2.28–1.08, 1.53* (d, 7 Hz, MeAla β-Me); 1.49° (d, 7 Hz, MeAla β-Me); 1.06* (d, 6.5 Hz, MeLeu d-Me); 0.98–0.82, 0.50' (d, Leu δ'-Me); 0.45* (d, 6.6 Hz, Leu δ'-Me); 0.28' (d, Leu δ"-Me); −0.11* (d, 6.6 Hz, Leu δ"-Me); −0.47* (ddd, Leu γ-CH).

35 (3 conformers 1:1:1): 8.62, 8.43, 8.07, 7.94, 7.87, 7.42 (6d, J=10 Hz, NH); 7.12 (d, J=7.4 Hz, indoline arom. H); 7.08–6.99 (m, indoline arom. H); 6.72, 6.69, (2dd indoline arom. H); 6.66–6.63 (m, indoline arom. H); 6.58 (d, J=8 Hz, indoline arom. H); 6.29 (d, J=8 Hz, Leu NH); 6.15 (m br, Leu NH); 5.88 (d, J=8 Hz, Leu NH); 5.28–4.98 (m, α-H); 4.93 (ddd, α-H); 4.74 (ddd, α-H); 4.65 (m, α-H); 4.54 (dd, α-H); 4.43 (dd, α-H); 3.80–3.66 (m); 3.55–3.0 (m); 3.46, 3.35, 3.31, 3.24, 3.22, 3.12, 3.00, 2.82, 2.57 (9s, N-Me); 2.55–1.1 (m); 1.52, 1.48, 1.43 (3d, J=7 Hz, MeAla β-Me); 1.13 (d, J=7 Hz); 1.03–0.83 (m); 0.78, 0.76, 0.73 (3d, J=6.5 Hz).

36 (3 conformers 73:23:4, marked with * ° '): 8.53* (d, J=10 Hz, PrLeu NH); 8.06* (d, J=10 Hz, PrLeu' NH); 7.95° (d, J=10 Hz, NH); 7.67*, 7.52° (2d, J=7 Hz, indole H-4'); 7.55* (d, J=10 Hz, NH); 7.33*, 7.31° (2d, J=8 Hz, indole H-7'); 7.19*, 7.17° (2dd, indole H-6'); 7.08*, 7.04° (2dd, indole H-5'); 6.98', 6.88°, 6.80* (3s, indole H-2'); 6.23° (d, J=9.3 Hz, Leu NH); 6.05* (d, J=7.5 Hz, Leu NH); 5.84' (d, Leu NH); 5.33° (ddd, PrLeu α-H); 5.18* (dd, Hba α-H); 5.14° (dd, Hba α-H); 5.05* (ddd, PrLeu α-H); 4.98° (ddd, Leu α-H); 4.93* (dd, indole α-H); 4.87* (ddd, PrLeu' α-H); 4.81° (ddd, Leu α-H); 4.47* (dd, MeLeu α-H); 4.22* (ddd Leu α-H); 3.86–3.67 (m); 3.83* (s, t-Bu-CH2-N); 3.69* (q, J=7 Hz, MeAla α-H); 3.5–3.2 (m); 3.43° (s, MeAla N-Me); 3.30* (s, MeAla N-Me); 3.22° (s, N-Me); 2.93* (s, MeMeTrp, N-Me); 2.53* (s, MeLeu N-Me); 2.53° (s, N-Me); 2.25 (m, Hba g-CH2); 2.18 (m, Hba β-Ha); 2.0–1.08 (m); 1.54*, 1.49° (2d, J=7 Hz, MeAla β-Ha); 1.05 (d, J=6.5 Hz, MeLeu Me);

0.97–0.84 (m); 0.52* (d, J=6.6 Hz, Leu Me); 0.28' (d); –0.06* (d, J=6.6 Hz, Leu Me); –0.49* (ddd, Leu γ-CH).

37 (3 conformers 78:19:3, marked with * ° '): 8.52* (d, 10 Hz, PrLeu6 NH); 8.06* (d, 10 Hz, PrLeu2 NH); 7.94° (d, 10 Hz, PrLeu NH); 7.68* (d, 8 Hz, indole H-4'); 7.53° (d, 8 Hz, indole H-4); 7.52° (d, 10 Hz, PrLeu NH); 7.36* (d, 8 Hz, indole H-7'); 7.33° (d, 8 Hz, indole H-7'); 7.2* (dd, indole H-6); 7.17° (dd, indole H-6'); 7.09* (dd, indole H-5'); 7.05° (dd, indole H-5'); 7.02° (s, indole H-2'); 6.91* (s, indole H-2'); 6.23° (d, 9.5 Hz, Leu NH); 6.03* (d, 7.4 Hz, Leu NH); 5.87' (d, Leu NH); 5.32° (ddd, PrLeu6 α-H); 5.18* (dd, Hba α-H); 5.14° (dd, Hba α-H); 5.05* (ddd, PrLeu6 α-H); 4.98° (ddd, PrLeu2 α-H); 4.93* (dd, MeTrp α-H); 4.87* (ddd, PrLeu2 α-H); 4.81° (ddd, Leu α-H); 4.60 (m, N-CH)4.46* (dd, MeLeu α-H); 4.16* (ddd, Leu α-H); 3.75° (q, 7 Hz, MeAla α-H); 3.70 (m); 3.69* (q, 7 Hz, MeAla α-H); 3.57° (dd, MeLeu α-H); 3.45 (m); 3.42° (s, MeAla N-Me); 3.32* (dd, MeTrp β-Ha); 3.31* (s, MeAla N-Me); 3.23* (dd, MeTrp β-Hb); 3.21° (s, N-Me); 2.93* (s, MeTrp N-Me); 2.53* (s, MeLeu N-Me); 2.50° (s, N-Me); 2.28 (AB-XY); 2.18 (AB-XY, Hba g-CH2); 2.13* (m, Hba γ-CHa); 1.93* (m, Hba γ-CHb); 1.85–1.08; 1.53* (d, 7 Hz, MeAla β-Me); 1.47 (m, N-CHMe2)1.04* (d, 6.5 Hz, MeLeu d-Me); 0.98–0.83; 0.52' (d, Leu δ'-Me); 0.51* (d, 6.6 Hz, Leu δ'-Me); 0.34' (d, Leu δ"-Me); –0.2* (d, 6.6 Hz, Leu δ"-Me); –0.60* (ddd, Leu γ-CH).

38 Indoline A (3 conformers 46:27:27, marked with * ° °): 8.62* (d, J=10 Hz, PrLeu NH); 8.13° (d, J=10 Hz, NH); 8.02° (d, J=10 Hz, NH); 7.92* (d, J=10 Hz, NH); 7.86* (d, J=10 Hz, PrLeu' NH); 7.40° (d, J=10 Hz, NH); 7.23° 7.16*, 7.09° (3d, J=7.4 Hz, indoline arom. H); 7.05°, 7.02*, 7.02' (3dd, indoline arom. H); 6.76°, 6.72*, 6.71° (3dd, indoline arom. H); 6.64°, 6.62°, 6.58* (3d, J=7.7 Hz, indoline arom. H); 6.32° (d, J=8 Hz, Leu NH); 6.10° (m br, Leu NH); 5.94* (d, J=9 Hz, Leu NH); 5.28–4.73 (m); 4.60° (dd, α-H); 4.13* (dd, α-H); 3.75–2.85 (m); 3.45*, 3.33°, 3.33*, 3.23°, 3.20°, 3.02*, 2.81°, 2.79*, 2.57° (9s, N-Me); 2.45–0.83 (m); 1.52°, 1.46°, 1.42* (3d, J=7 Hz, MeAla β-Me).Indoline B (3 conformers 1:1:1): 8.62, 8.43, 8.07, 7.94, 7.87, 7.42 (6d, J=10 Hz, NH); 7.12 (d, J=7.4 Hz, indoline arom. H); 7.08–6.99 (m, indoline arom. H); 6.72, 6.69, (2dd indoline arom. H); 6.66–6.63 (m, indoline arom. H); 6.58 (d, J=8 Hz, indoline arom. H); 6.29 (d, J=8 Hz, Leu NH); 6.15 (m br, Leu NH); 5.88 (d, J=8 Hz, Leu NH); 5.28–4.98 (m, α-H); 4.93 (ddd, α-H); 4.74 (ddd, α-H); 4.65 (m, α-H); 4.54 (dd, α-H); 4.43 (dd, α-H); 3.80–3.66 (m); 3.55–3.0 (m); 3.46, 3.35, 3.31, 3.24, 3.22, 3.12, 3.00, 2.82, 2.57 (9s, N-Me); 2.55–1.1 (m); 1.52, 1.48, 1.43 (3d, J=7 Hz, MeAla β-Me); 1.13 (d, J=7 Hz); 1.03–0.83 (m); 0.78, 0.76, 0.73 (3d, J=6.5 Hz).

39 (3 conformers 76:18:6, marked with * ° '): 8.49* (d, 10 Hz, PrLeu6 NH); 8.05* (d, 10 Hz, PrLeu2 NH); 7.94° (d, 10 Hz, PrLeu6 NH); 7.67* (d, 8 Hz, indole H-4'); 7.53° (d, 8 Hz, indole H-4'); 7.52° (d, 10 Hz, PrLeu2 NH); 7.4* (d, 8 Hz, indole H-7'); 7.38° (d, 8 Hz, indole H-7'); 7.23* (dd, indole H-6'); 7.19° (dd, indole H-6'); 7.11* (dd, indole H-5'); 7.07° (dd, indole H-5'); 7.05° (s, indole H-2'); 7.01* (s, indole H-2'); 6.22° (d, br, Leu NH); 6.05* (d, 7.5 Hz, Leu NH); 5.84' (d, Leu NH); 5.31° (ddd, PrLeu6 α-H); 5.19* (dd, Hba α-H); 5.16° (dd, Hba α-H); 5.04* (ddd, PrLeu6 α-H); 5.00° (ddd, PrLeu2 α-H); 4.94* (dd, MeTrp α-H); 4.87* (ddd, PrLeu2 α-H); 4.81° (ddd, Leu α-H); 4.67' (ddd, Leu α-H); 4.45* (dd, MeLeu α-H); 4.18* (ddd, Leu α-H); 4.14 (s, OPr); 3.80–3.55; 3.67* (q, 7 Hz, MeAla α-H); 3.50–3.40; 3.42° (s, MeAla N-Me); 3.29* (dd, MeTrp β-Ha); 3.27* (s, MeAla N-Me); 3.21° (s, N-Me); 3.18* (dd, MeTrp β-Hb); 3.04' (s, N-Me); 2.93* (s, MeTrp N-Me); 2.55° (s, N-Me); 2.53* (s, MeLeu N-Me); 2.30–1.90; 1.80 (m, OPr); 1.53* (d, 7 Hz, MeAla β-Me); 1.48° (d, 7 Hz, MeAla β-Me); 1.08° (t, OPr); 1.07 (t, OPr); 1.05* (d, 6.5 Hz, MeLeu d-Me); 0.98–0.85; 0.59' (d, Leu δ'-Me); 0.57* (d, 6.6 Hz, Leu δ'-Me); 0.37' (d, Leu δ"-Me); –0.07* (d, 6.6 Hz, Leu δ"-Me).

40 (3 conformers 73:21:6, marked with * ° '): 8.49* (d, 10 Hz, PrLeu6 NH); 8.05* (d, 10 Hz, PrLeu2 NH); 7.94° (d, 10 Hz, PrLeu6 NH); 7.67* (d, 8 Hz, indole H-4'); 7.53(d, 8 Hz, indole H-4'); 7.52° (d, 10 Hz, PrLeu2 NH); 7.4* (d, 8 Hz, indole H-7'); 7.38° (d, 8 Hz, indole H-7'); 7.23* (dd, indole H-6'); 7.19° (dd, indole H-6'); 7.11* (dd, indole H-5'); 7.07° (dd, indole H-5'); 7.05° (s, indole H-2'); 7.01* (s, indole H-2'); 6.22° (d, 9.4 Hz, Leu NH); 6.05* (d, 7.3 Hz, Leu NH); 5.86' (d, Leu NH); 5.31° (ddd, PrLeu6 α-H); 5.19* (dd, Hba α-H); 5.16° (dd, Hba α-H); 5.03* (ddd, PrLeu6 α-H); 5° (ddd, PrLeu2 α-H); 4.94* (dd, MeTrp α-H); 4.87* (ddd, PrLeu2 α-H); 4.81° (ddd, Leu α-H); 4.65' (ddd, Leu α-H); "4.46* (dd, MeLeu α-H); 4.26* (q, OEt); 4.26° (q, OEt); 4.19* (ddd, Leu α-H); 3.80–3.56; 3.67* (q, 7 Hz, MeAla α-H); 3.45–3.33; 3.41° (s, MeAla N-Me); 3.29* (dd, MeTrp β-Ha); 3.27* (s, MeAla N-Me); 3.21° (s, N-Me); 3.19* (dd, MeTrp β-Hb); 3.04' (s, N-Me); 2.93* (s, MeTrp N-Me); 2.57° (s, N-Me); 2.52* (s, MeLeu N-Me); 2.32–1.08; 1.53* (d, 7 Hz, MeAla β-Me); 1.48° (d, 7 Hz, MeAla β-Me); 1.40° (t, OEt); 1.40* (t, OEt); 1.05* (d, 6.5 Hz, MeLeu d-Me); 0.98–0.84; 0.60' (d, Leu δ'-Me); 0.57* (d, 6.6 Hz, Leu δ'-Me); 0.37' (d, Leu δ"-Me); –0.07* (d, 6.6 Hz, Leu δ"-Me); –0.36* (ddd, Leu γ-CH).

41 (3 conformers 63:32:5, marked with * ° '): 8.45* (d, 10 Hz, PrLeu6 NH); 8.06* (d, 10 Hz, PrLeu2 NH); 7.97° (d, 10 Hz, PrLeu6 NH); 7.90' (d, 10 Hz, PrLeu6 NH); 7.63* (d, 8 Hz, indole H-4'); 7.56° (d, 10 Hz, PrLeu2 NH); 7.45° (d, 8 Hz, indole H-4'); 7.4 (d, 8 Hz, indole H-7'); 7.38° (d, 8 Hz, indole H-7); 7.23* (dd, indole H-6'); 7.22° (dd, indole H-6'); 7.13* (dd, indole H-5'); 7.08° (dd, indole H-5'); 6.2° (d, 10 Hz, Leu NH); 6.07* (d, 7.5 Hz, Leu NH); 5.77' (d, 8.5 Hz, Leu NH); 5.32° (ddd, PrLeu6 α-H); 5.26' (dd, Hba α-H); 5.2* (dd, Hba α-H); 5.16° (dd, Hba α-H); 5.03* (ddd, PrLeu6 α-H); 4.97* (dd, MeTrp α-H); 4.87* (ddd, PrLeu2 α-H); 4.67° (ddd, α-H); 4.46* (dd, MeLeu α-H); 4.13* (ddd, Leu α-H); 4.09* (s, N-OMe); 4.04' (s, N-OMe); 4.03° (s, N-OMe); 3.74° (q, 7 Hz, MeAla α-H); 3.71* (q, 7 Hz, MeAla α-H); 3.70–3.60; 3.54–3.50; 3.47° (s, MeAla N-Me); 3.28–3.17; 3.25* (s, MeAla N-Me); 3.20° (s, N-Me); 2.97* (s, MeTrp N-Me); 2.52* (s, MeLeu N-Me); 2.42° (s, N-Me); 2.40–2.14; 1.97 (m); 1.79 (m); 1.65–1.08; 1.53* (d, 7 Hz, MeAla β-Me); 1.5° (d, 7 Hz, MeAla β-Me); 1.04* (d, 6.5 Hz, MeLeu d-Me); 0.98–0.83; 0.62' (d, Leu δ'-Me); 0.57* (d, 6.6 Hz, Leu δ'-Me); 0.37' (d, Leu δ"-Me); –0.09* (d, 6.6 Hz, Leu δ"-Me); –0.35* (ddd, Leu γ-CH).

42 (3 conformers 44:30:26, marked with *°'): 8.85 (d, CSNH2); 8.6 (d, PrLeu6 NH); 8.17 (d, CSNH2); 8.03, 8.00 (2d, NH); 7.88 (m, CSNH2); 7.6–7.1; 6.28* (d, 10 Hz, Leu NH); 6.07* (d, 7 Hz, Leu NH); 5.87' (d, 9 Hz, Leu NH); 6.26* (ddd, PrLeu2 α-H), 5.22 (dd, Hba α-H); 5.15–4.95, 5.08* (dd, Hba α-H); 4.83° (ddd, PrLeu2 α-H); 4.50* (ddd, Leu α-H); 4.37* (dd, MeTrp α-H); 4.25° (ddd, Leu α-H); 4.09, 4.05, 4.03* (3s, OMe); 3.89 (m, α-H); 3.65*, 3.63', 3.52° (3q, 7 Hz, MeAla α-H); 3.57 (m), 3.17, 3.16, 3.15, 3.22, 3.20, 3.05, 2.92, 2.55, 2.53 (9s, NMe); 1.8–1.1; 1.05 (d, 7 Hz); 0.99–0.82, 0.60°, 0.55', 0.23°, 0.17° (4d, 7 Hz, Leu δ-Me); –0.15°, –0.17' (ddd, Leu γ-CH).

I claim:
1. A cyclopeptolide of formula I

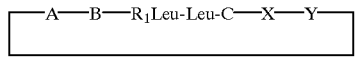

wherein:
A is an α-hydroxy-substituted butyric acid residue optionally γ-substituted by $R_6$, which represents CN, $COOR_2$, $CONR_3R_4$, $COR_5$, $CSNH_2$ or alkyl, which may be substituted by azido, halogen, alkoxy, optionally protected hydroxy or amino, vinyl, which may be substituted by alkyl, halogen or CN, cycloalkyl, tetrazolyl or —C≡CH, wherein $R_2$ represents hydrogen or optionally arylsubstituted alkyl, $R_3$ and $R_4$ are the same or different and represent hydrogen or alkyl or form together with the nitrogen a 3- to 6-membered ring optionally containing a second heteroatom, and $R_5$ represents hydrogen or lower alkyl, B is an α-amino-γ-methyl-substituted octanoic acid residue;

$R_1$ is hydrogen or methyl;

C is a tryptophan or N-methyl-tryptophan residue of formula VI

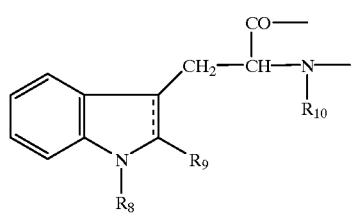

wherein $R_8$ represents hydrogen, alkoxy, alkyl or benzyl, $R_9$ represents hydrogen or halogen, $R_{10}$ represents hydrogen or methyl and ---- represents a single or double bond, X is an α-amino-substituted ($C_2$ to $C_{14}$) carboxylic acid residue, and Y is an α-amino- or N-methyl-α-amino substituted ($C_2$ to $C_{10}$) carboxylic acid residue.

2. A cyclopeptolide according to claim 1, in which A is an α-hydroxybutyric acid residue, which is γ-substituted by cyano, $COOR_2'$, whererby $R_2'$ represents hydrogen, lower alkyl with 1 to 4 carbon atoms or diphenylmethyl, $CONR_3'R_4'$, whereby $R_3'$ represents hydrogen or methyl and $R_4'$ represents hydrogen or alkyl or $R_3'$ and $R_4'$ form together with the nitrogen a 3- to 6-membered ring or a morpholinyl ring, $CH_2OH$, $COR_5'$, whereby $R_5'$ represents hydrogen or lower alkyl with 1 to 4 carbon atoms, vinyl optionally substituted by CN, Br or lower alkyl with 1 to 4 carbon atoms, alkyl optionally substituted by azido, amino, hydroxy, chloro or alkoxy, tetrazolyl, cyclopropyl, $CSNH_2$ or —C≡CH.

3. A cyclopeptolide according to claim 1 or 2, in which C is a N-methyltryptophan residue of formula VI, wherein $R_8$ represents hydrogen, ($C_1$ to $C_4$)alkoxy, especially methoxy, or alkyl and $R_9$ represents hydrogen or halogen.

4. A cyclopeptolide according to claim 1, in which X is an α-amino-substituted ($C_4$ to $C_8$) carboxylic acid residue, which is optionally β- or γ-($C_1$ to $C_4$) alkyl substituted.

5. A cyclopeptolide according to claim 4, in which X is an α-amino-β- or γ-($C_1$ to $C_4$) alkyl, substituted octanoic or a butyric acid residue.

6. A cyclopeptolide according to claim 1 in which Y is an N-methyl-α-amino-substituted ($C_2$ to $C_4$) carboxylic acid residue, which is optionally β- or γ-($C_1$ to $C_4$) alkyl substituted.

7. A cyclopeptolide according to claim 5, in which Y is an N-methyl-alanine or N-methyl valine residue.

8. A cyclopeptolide of formula II

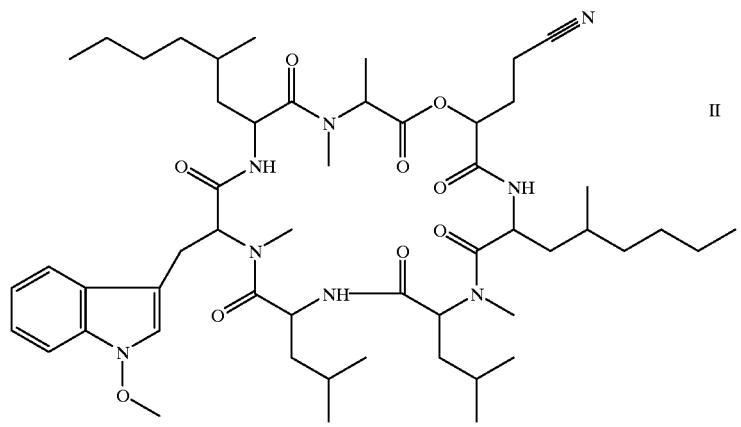

9. A cyclopeptolide of formula III

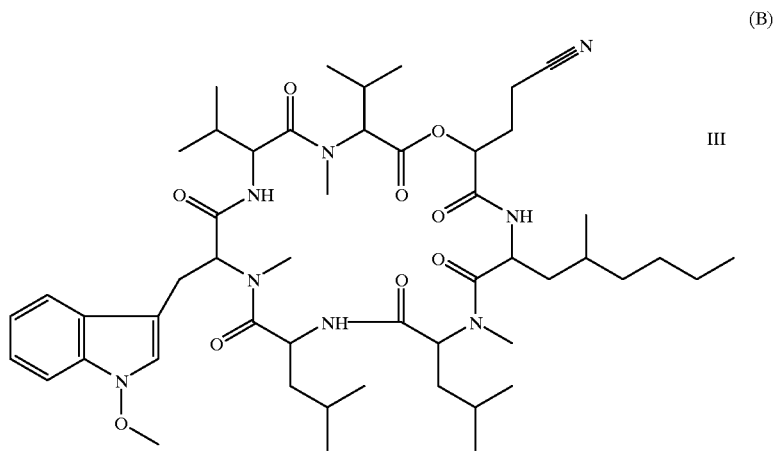

10. An open-chain peptolide which corresponds to a cyclopeptolide according to claim 1 wherein the open-chain peptolide is obtained either by cleavage of the ester bond between residues Y and A or by cleavage of an amide linkage between any other adjacent pair of acid residues.

11. An open chain peptolide of formula IV

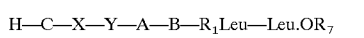

wherein the substituents are as defined in claim 1 and $R_7$ represents hydrogen or alkyl.

12. An open chain peptolide of formula V

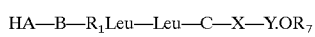

wherein the substituents are as defined in claim 1 and $R_7$ represents hydrogen or alkyl.

13. A cyclopeptolide of formula Ip

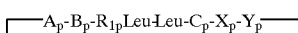

wherein:

$A_p$ is an α-hydroxy-substituted butyric acid residue optionally γ-substituted by $R_{6p}$, which represents CN, optionally protected $CH_2OH$, $COOR_{2p}$, $CONR_{3p}R_{4p}$, $COR_{5p}$ or —CH=$CH_2$, whereby $R_{2p}$ represents hydrogen or optionally arylsubstituted alkyl, $R_{3p}$ and $R_{4p}$ are the same or different and represent hydrogen or alkyl or form together with the nitrogen a 5- or 6-membered ring optionally containing a second heteroatom, and $R_{5p}$ represents hydrogen or lower alkyl, $B_p$ is an α-amino-γ-methyl-substituted octanoic acid residue;

$R_{1p}$ is hydrogen or methyl;

$C_p$ is a tryptophan or N-methyl-tryptophan residue, which is optionally N'-($C_1$ to $C_4$) alkoxy substituted;

$X_p$ is an α-amino-substituted ($C_2$ to $C_{14}$) carboxylic acid residue, and $Y_p$ is an α-amino- or N-methyl-α-amino substituted ($C_2$ to $C_{10}$) carboxylic acid residue.

14. A cyclopeptolide of formula I'p

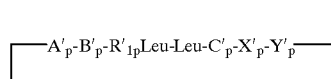

wherein:

$A'_p$ is an α-hydroxy-substituted butyric acid residue optionally γ-substituted by $R'_{6p}$, which represents CN, $COOR'_{2p}$, $CONR'_{3p}R'_{4p}$, $COR'_{5p}$, alkyl, which may be substituted by azido, halogen, alkoxy, optionally protected hydroxy or amino, vinyl, which may be substituted by alkyl, halogen or CN, cycloalkyl, tetrazolyl or —C≡CH, whereby $R'_{2p}$ represents hydrogen or optionally arylsubstituted alkyl, $R'_{3p}$ and $R'_{4p}$ are the same or different and represent hydrogen or alkyl or form together with the nitrogen a 3- to 6-membered ring optionally containing a second heteroatom, and $R'_{5p}$ represents hydrogen or lower alkyl, $B'_p$ is an α-amino-γ-methyl-substituted octanoic acid residue;

$R'_{1p}$ is hydrogen or methyl;

$C'_p$ is a tryptophan or N-methyl-tryptophan residue of formula VI'p

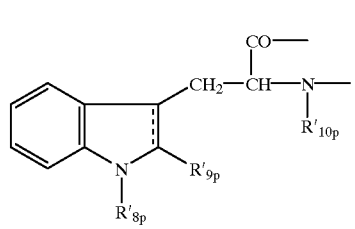

wherein $R'_{8p}$ represents hydrogen, alkoxy, alkyl or benzyl, $R'_{9p}$ represents hydrogen or halogen, $R'_{10p}$ represents hydrogen or methyl and ---- represents a single or double bond, $X'_p$ is an α-amino-substituted ($C_2$ to $C_{14}$) carboxylic acid residue, and $Y'_p$ is an α-amino- or N-methyl-α-amino substituted ($C_2$ to $C_{10}$) carboxylic acid residue.

15. A compound according to claim 1 in salt or ester form.

16. Fungal strain F92-4471/08 deposited as NRRL 21123.

17. Cyclopeptolides according to claim 1 which are produced by Strain F92-4471/08 deposited as NRRL 21123.

18. A process for the preparation of a compound according to claim 1 which comprises cultivating F92-4471/08 (NRRL 21123) or a similar fungal species in nutrient medium and recovering the compound therefrom.

19. A process for the preparation of a compound according to claim 1 by derivatisation of a compound of formula II or III, which comprises a)—for the preparation of compounds of formula 1, wherein $R_6$ represents $COOR_2'$, whereby $R_2'$ is alkyl optionally substituted by aryl, reacting compounds of formula 1, wherein $R_6$ represents CN, with nucleophiles, with appropriate basic or acidic catalysis, in organic solvents, or b)—for the preparation of compounds of formula 1, wherein $R_6$ represents COAlkyl, reacting compounds of formula I, wherein $R_6$ represents CN, using as nucleophiles organo-metallic compounds, which are reacted in aprotic organic solvents, with or without catalysts, or c)—for the preparation of compounds of formula I, wherein $R_6$ represents COOH, hydrolyzing compounds of formula I, wherein $R_6$ represents COAlkyl, with mineral acid or base, or d)—for the preparation of compounds of formula I, wherein $R_6$ represents $COOR_2'$, esterifying compounds of formula I, wherein $R_6$ represents COOH, by standard methods, or e)—for the preparation of compounds of formula I, wherein $R_6$ represents $CH_2OH$, reducing compounds of formula I, wherein $R_6$ represents $COOR_2$, with metal hydrides or boron hydrides in organic solvents, or f)—for the preparation of compounds of formula I, wherein $R_6$ represents $CONR_3R_4$, transforming compounds of formula I, wherein $R_6$ represents $COOR_2$, by reaction with amines, or g)—for the preparation of compounds of formula I, wherein $R_6$ represents CHO, oxidizing compounds of formula I, wherein $R_6$ represents $CH_2OH$, or h)—for the preparation of compounds of formula I, wherein $R_6$ represents optionally substituted vinyl, reacting compounds of formula I, wherein $R_6$ represents CHO, with a methyl-Wittig reagent, or i)—for the preparation of compounds of formula I, wherein $R_6$ represents optionally substituted alkyl, reacting compounds of formula I, wherein $R_6$ represents $CH_2OH$, or j)—for the preparation of compounds of formula I, wherein $R_6$ represents $CH_2NH_2$, reducing compounds of formula I, wherein $R_6$ represents $CH_2N_3$, or k)—for the preparation of compounds of formula I, wherein $R_6$ represents C≡CH, reacting compounds of formula I, wherein $R_6$ represents $CH=CBr_2$, or l)—for the preparation of compounds of formula I, wherein $R_6$ represents cyclopropyl, reacting compounds of formula I, wherein $R_6$ represents vinyl, with diazomethane, or m)—for the preparation of compounds of formula I, wherein $R_6$ represents tetrazolyl, reacting compounds of formula I, wherein $R_6$ is CN, with an azide-compound, or n)—for the preparation of compounds of formula I, wherein $R_8$ represents hydrogen, removing the methoxy from compounds of formula I, wherein $R_8$ represents $OCH_3$, or o)—for the preparation of compounds of formula I, wherein the symbol ---- represents a single bond, reducing compounds of formula I, wherein the symbol ---- represents a double bond, or p)—for the preparation of compounds of formula I, wherein $R_8$ represents alkyl or benzyl, introducing these groups into compounds of formula I, wherein $R_8$ represents hydrogen, or q)—for the preparation of compounds of formula I, wherein $R_9$ represents halogen, halogenating compounds of formula I, wherein $R_9$ represents hydrogen, or r)—for the preparation of compounds of formula I, wherein $R_8$ represents alkoxy and the symbol ---- represents a double bond, reacting compounds of formula I, wherein $R_8$ represents hydrogen and the symbol ---- represents a single bond, with an alkalitungstate and hydrogen peroxide and alkylating the N-hydroxy-indol-intermediate, or s)—for the preparation of compounds of formula I1, wherein $R_6$ represents $CSNH_2$, reacting compounds of formula I with sulfur derivatives.

20. A process for the preparation of a compound according to claim 1 comprising cyclising a linear peptide or peptolide comprising the acid residues A, B, $R_1$Leu, Leu, C, X, and Y linked together in appropriate order.

21. Therapeutic use of a compound according to claim 1.

22. A therapeutic composition comprising a therapeutically effective amount of a compound according to claim 1.

23. A therapeutic composition according to claim 22 in the form of a cream or lotion or the like for topical use.

24. A therapeutic composition according to claim 22 in the form of an aerosol for use with an inhaler.

25. A method of inhibiting adhesion molecule expression comprising administering to a patient in need of such inhibition an inhibiting effective amount of a compound according to claim 1.

26. A method for the treatment or prophylaxis of a disease which involves elevated levels of adhesion molecule expression comprising administering to a patient in need of such treatment or prophylaxis an effective amount of a compound according to claim 1.

27. A cyclopeptolide according to claim 5 wherein said ($C_1$ to $C_4$) alkyl is methyl.

28. A compound having a $[\alpha]_D^{25}$ of −234° (MeOH, c=1.11), a mass spectrum having an m/e=977($MH^+$), a UV spectrum (MeOH) corresponding to FIG. 1a, and a $^{13}CNMR$ corresponding to FIG. 6.

29. A compound having a $[\alpha]_D^{25}$ of $-242°$ (MeOH, c=1.08), a mass spectrum having an m/e=949(MH$^+$), a UV spectrum (MeOH) corresponding to FIG. 1b, and a $^{13}$CNMR corresponding to FIG. 7.
30. A compound according to claim 1 wherein
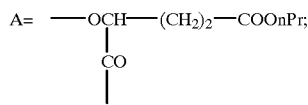
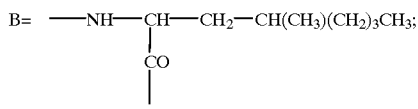
$R_1 = CH_3$;
-continued
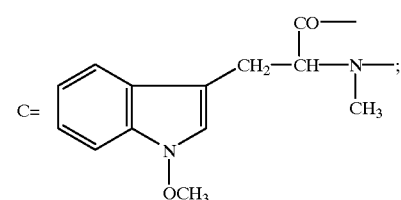
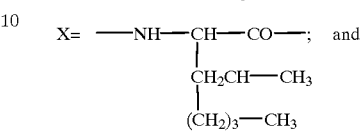  and
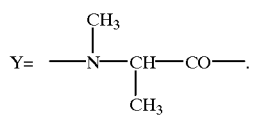
* * * * *

UNITED STATES PATENT AND TRADEMARK OFFICE
CERTIFICATE OF CORRECTION

PATENT NO. : 6,013,627
DATED : January 11, 2000
INVENTOR(S) : DREYFUSS ET AL.

It is certified that error appears in the above-indentified patent and that said Letters Patent is hereby corrected as shown below:

In the claims, under column 39, claim 19, paragraph c), 3rd line, "COAlkyl" should be deleted and replaced with -- COOAlkyl -- .

Signed and Sealed this

Third Day of April, 2001

Attest:

NICHOLAS P. GODICI

*Attesting Officer*    *Acting Director of the United States Patent and Trademark Office*